US011707351B2

(12) United States Patent
Jones et al.

(10) Patent No.: US 11,707,351 B2
(45) Date of Patent: Jul. 25, 2023

(54) EMBOLIC PROTECTION AND ACCESS SYSTEM

(71) Applicant: ENCOMPASS TECHNOLOGIES, INC., Carson City, NV (US)

(72) Inventors: Michael Jones, San Clemente, CA (US); George Wallace, San Clemente, CA (US); Brady Haug, San Clemente, CA (US)

(73) Assignee: ENCOMPASS TECHNOLOGIES, INC., Carson City, NV (US)

( * ) Notice: Subject to any disclaimer, the term of this patent is extended or adjusted under 35 U.S.C. 154(b) by 21 days.

(21) Appl. No.: 16/996,657

(22) Filed: Aug. 18, 2020

(65) Prior Publication Data
US 2021/0052360 A1     Feb. 25, 2021

Related U.S. Application Data

(63) Continuation-in-part of application No. 16/868,076, filed on May 6, 2020.
(Continued)

(51) Int. Cl.
*A61F 2/01*     (2006.01)
*A61F 2/24*     (2006.01)

(52) U.S. Cl.
CPC ............ *A61F 2/013* (2013.01); *A61F 2/2439* (2013.01); *A61F 2002/016* (2013.01); *A61F 2002/018* (2013.01)

(58) Field of Classification Search
None
See application file for complete search history.

(56) References Cited

U.S. PATENT DOCUMENTS

| 6,139,517 A | 10/2000 | Macoviak et al. |
| 6,254,563 B1 | 7/2001 | Macoviak et al. |

(Continued)

FOREIGN PATENT DOCUMENTS

| EP | 0 980 278 | 9/2004 |
| EP | 1 059 890 | 12/2004 |

(Continued)

OTHER PUBLICATIONS

International Search Report and Written Opinion, for PCT/US2020/031887, dated Sep. 2, 2020.
(Continued)

*Primary Examiner* — Tan-Uyen T Ho
*Assistant Examiner* — David P Stein
(74) *Attorney, Agent, or Firm* — Knobbe, Martens, Olson & Bear, LLP

(57) ABSTRACT

Methods and devices are provided for protecting the cerebrovascular circulation from embolic debris released during an index procedure. An embolic protection filter is delivered in a reduced profile configuration via an access catheter, and positioned in the aorta spanning the ostia to the three great vessels leading to the cerebral circulation. An index procedure catheter is thereafter advanced through the same access catheter to conduct the index procedure. The index procedure may be a transcatheter aortic valve replacement. A pore distribution in the filter blocks passage of debris greater than a predetermined threshold, minimizes total cumulative volume of debris passing through the filter and minimizes blood pressure drop across the filter.

20 Claims, 16 Drawing Sheets

Related U.S. Application Data

(60) Provisional application No. 62/888,897, filed on Aug. 19, 2019.

(56) References Cited

U.S. PATENT DOCUMENTS

| | | |
|---|---|---|
| 6,258,120 B1 | 7/2001 | McKenzie et al. |
| 6,277,138 B1 | 8/2001 | Levinson et al. |
| 6,361,545 B1 | 3/2002 | Macoviak et al. |
| 6,395,014 B1 | 5/2002 | Macoviak et al. |
| 6,499,487 B1 | 12/2002 | McKenzie et al. |
| 6,508,826 B2 | 1/2003 | Murphy et al. |
| 6,547,760 B1 | 4/2003 | Samson et al. |
| 6,663,652 B2 | 12/2003 | Daniel et al. |
| 6,676,683 B1 | 1/2004 | Addis |
| 6,682,543 B2 | 1/2004 | Barbut et al. |
| 6,689,152 B2 | 2/2004 | Balceta et al. |
| 6,719,775 B2 | 4/2004 | Slaker et al. |
| 6,726,701 B2 | 4/2004 | Gilson et al. |
| 6,743,246 B1 | 6/2004 | Maahs |
| 6,840,950 B2 | 1/2005 | Stanford et al. |
| 6,936,059 B2 | 8/2005 | Belef |
| 6,953,471 B1 | 10/2005 | Lilly et al. |
| 6,969,396 B2 | 11/2005 | Krolik et al. |
| 7,001,406 B2 | 2/2006 | Eskuri et al. |
| 7,011,672 B2 | 3/2006 | Barbut et al. |
| 7,112,213 B2 | 9/2006 | Maahs |
| 7,118,539 B2 | 10/2006 | Vrba et al. |
| 7,118,585 B2 | 10/2006 | Addis |
| 7,137,991 B2 | 11/2006 | Fedie |
| 7,163,550 B2 | 1/2007 | Boismier |
| 7,229,454 B2 | 6/2007 | Tran et al. |
| 7,232,453 B2 | 6/2007 | Shimon |
| 7,247,162 B1 | 7/2007 | Thornton |
| 7,252,675 B2 | 8/2007 | Denison et al. |
| 7,323,001 B2 | 1/2008 | Clubb et al. |
| 7,455,737 B2 | 11/2008 | Boismier et al. |
| 7,459,080 B2 | 12/2008 | Lowe et al. |
| 7,479,153 B2 | 1/2009 | Belef |
| 7,481,823 B2 | 1/2009 | Broome et al. |
| 7,537,600 B2 | 5/2009 | Eskuri |
| 7,588,780 B2 | 9/2009 | Buiser et al. |
| 7,608,087 B1 | 10/2009 | Addis |
| 7,651,514 B2 | 1/2010 | Salahieh et al. |
| 7,666,179 B2 | 2/2010 | Tenney et al. |
| 7,686,783 B2 | 3/2010 | Jenson et al. |
| 7,717,935 B2 | 5/2010 | Tsugita et al. |
| 7,737,060 B2 | 6/2010 | Strickler et al. |
| 7,780,696 B2 | 8/2010 | Daniel et al. |
| 7,857,826 B2 | 12/2010 | Eskuri et al. |
| 7,879,062 B2 * | 2/2011 | Galdonik ............ A61F 2/01 606/200 |
| 7,998,163 B2 | 8/2011 | Salahieh et al. |
| 8,025,674 B2 | 9/2011 | Barbut et al. |
| 8,038,709 B2 | 10/2011 | Palasis et al. |
| 8,048,103 B2 | 11/2011 | Salahieh |
| 8,052,717 B2 | 11/2011 | Mujkanovic |
| 8,062,324 B2 | 11/2011 | Shimon et al. |
| 8,070,769 B2 | 12/2011 | Broome |
| 8,109,962 B2 | 2/2012 | Pal |
| 8,114,114 B2 | 2/2012 | Belson |
| 8,123,779 B2 | 2/2012 | Demond et al. |
| 8,152,833 B2 | 4/2012 | Zaver et al. |
| 8,197,527 B2 | 6/2012 | Borillo et al. |
| 8,206,403 B2 | 6/2012 | Thornton |
| 8,231,651 B2 | 7/2012 | Tsugita |
| 8,236,024 B2 | 8/2012 | Stanford et al. |
| 8,308,754 B2 | 11/2012 | Belson |
| 8,337,519 B2 | 12/2012 | Wasicek |
| 8,353,951 B2 | 1/2013 | Frid |
| 8,394,119 B2 | 3/2013 | Zaver et al. |
| 8,409,238 B2 | 4/2013 | Renati et al. |
| 8,409,240 B2 | 4/2013 | Tripp et al. |
| 8,409,242 B2 | 4/2013 | Clubb et al. |
| 8,414,482 B2 | 4/2013 | Belson |
| 8,430,904 B2 | 4/2013 | Belson |
| 8,679,149 B2 | 3/2014 | Belson |
| 8,728,114 B2 | 5/2014 | Belson |
| 8,734,829 B2 | 5/2014 | Weber |
| 8,840,636 B2 | 9/2014 | Barbut et al. |
| 8,852,225 B2 | 10/2014 | Shu et al. |
| 8,882,782 B2 | 11/2014 | Thornton |
| 8,948,848 B2 | 2/2015 | Merhi |
| 8,968,354 B2 | 3/2015 | Wang et al. |
| 8,974,490 B2 | 3/2015 | Jonsson |
| 9,023,101 B2 | 5/2015 | Krahbichler |
| 9,107,734 B2 | 8/2015 | Belson |
| 9,186,238 B2 | 11/2015 | Eidenschink et al. |
| 9,211,179 B2 | 12/2015 | Schotzko et al. |
| 9,339,367 B2 | 5/2016 | Carpenter et al. |
| 9,370,438 B2 | 6/2016 | Ginn |
| 9,452,040 B2 | 9/2016 | Arcand et al. |
| 9,480,548 B2 | 11/2016 | Carpenter et al. |
| 9,480,561 B2 | 11/2016 | Eidenschink |
| 9,492,265 B2 | 11/2016 | Russell et al. |
| 9,498,225 B2 | 11/2016 | Zhadkevich |
| 9,566,144 B2 | 2/2017 | Purcell et al. |
| 9,579,182 B2 | 2/2017 | Krahbichler |
| 9,603,692 B2 | 3/2017 | Clubb et al. |
| 9,668,849 B2 | 6/2017 | Shimon |
| 9,770,318 B2 | 9/2017 | Belson |
| 9,782,247 B2 | 10/2017 | Grewe |
| 9,827,085 B2 | 11/2017 | Russell et al. |
| 9,844,387 B2 | 12/2017 | Marchand et al. |
| 9,877,821 B2 | 1/2018 | Russell et al. |
| 9,888,994 B2 | 2/2018 | Lees et al. |
| 9,888,995 B2 | 2/2018 | Lees et al. |
| 9,895,216 B2 | 2/2018 | Golan |
| 9,968,433 B2 | 5/2018 | Adams et al. |
| 10,016,267 B2 | 7/2018 | Belson |
| 10,064,637 B2 | 9/2018 | Zandi et al. |
| 10,076,335 B2 | 9/2018 | Zaver et al. |
| 10,076,400 B2 | 9/2018 | Krahbichler |
| 10,130,371 B2 | 11/2018 | Dehdashtian et al. |
| 10,166,094 B2 | 1/2019 | Russell et al. |
| 10,213,288 B2 | 2/2019 | Johnson et al. |
| 10,335,259 B2 | 7/2019 | Frid |
| 10,342,571 B2 | 7/2019 | Marchand et al. |
| 10,426,591 B2 | 10/2019 | Carpenter et al. |
| 10,433,946 B2 | 10/2019 | Krahbichler |
| 10,433,988 B2 | 10/2019 | Zaver et al. |
| 10,485,647 B2 | 11/2019 | Gera et al. |
| 10,500,033 B2 | 12/2019 | Naor et al. |
| 10,512,479 B2 | 12/2019 | Nguyen et al. |
| 10,617,507 B2 | 4/2020 | Belson |
| 10,617,509 B2 | 4/2020 | Kleshinski et al. |
| 10,617,510 B2 | 4/2020 | Russell et al. |
| 10,624,732 B2 | 4/2020 | Shimon |
| 10,675,139 B2 | 6/2020 | Von Mangoldt et al. |
| 10,687,931 B2 | 6/2020 | Bearnson |
| 10,695,175 B2 | 6/2020 | Delaloye et al. |
| 10,736,728 B2 | 8/2020 | Belson |
| 10,751,158 B2 | 8/2020 | Sutton et al. |
| 10,842,609 B2 | 11/2020 | Mustapha |
| 10,881,494 B2 | 1/2021 | Belson |
| 10,918,389 B2 | 2/2021 | Berez et al. |
| 10,939,987 B2 | 3/2021 | Belson |
| 10,966,811 B2 | 4/2021 | Verin et al. |
| 11,051,927 B2 | 7/2021 | Russell et al. |
| 11,071,844 B2 | 7/2021 | Merhi et al. |
| 11,284,986 B2 | 3/2022 | Lee et al. |
| 11,304,792 B2 | 4/2022 | Russell et al. |
| 11,389,284 B2 | 7/2022 | Lenneman et al. |
| 11,399,927 B2 | 8/2022 | Kleshinski et al. |
| 11,439,491 B2 | 9/2022 | Hamill et al. |
| 2002/0010411 A1 | 1/2002 | Macoviak et al. |
| 2002/0077596 A1 | 6/2002 | McKenzie et al. |
| 2002/0128680 A1 | 9/2002 | Pavlovic |
| 2002/0143362 A1 | 10/2002 | Macoviak et al. |
| 2003/0055452 A1 | 3/2003 | Joergensen et al. |
| 2003/0100940 A1 | 5/2003 | Yodfat |
| 2003/0158571 A1 | 8/2003 | Esch et al. |
| 2003/0158574 A1 | 8/2003 | Esch et al. |
| 2003/0236496 A1 | 12/2003 | Samson et al. |

(56) References Cited

U.S. PATENT DOCUMENTS

| | | |
|---|---|---|
| 2004/0051201 A1 | 3/2004 | Greehalgh et al. |
| 2004/0153117 A1* | 8/2004 | Clubb ............... D04C 3/48 606/200 |
| 2005/0267516 A1 | 12/2005 | Soleimani et al. |
| 2006/0015138 A1* | 1/2006 | Gertner ............... A61F 2/01 606/200 |
| 2006/0161241 A1 | 7/2006 | Barbut et al. |
| 2006/0253148 A1 | 11/2006 | Leone et al. |
| 2006/0287668 A1 | 12/2006 | Fawzi et al. |
| 2006/0293706 A1 | 12/2006 | Shimon |
| 2008/0004687 A1 | 1/2008 | Barbut et al. |
| 2008/0140110 A1 | 6/2008 | Spence |
| 2010/0179583 A1 | 7/2010 | Carpenter et al. |
| 2010/0179584 A1 | 7/2010 | Carpenter et al. |
| 2010/0179647 A1 | 7/2010 | Carpenter et al. |
| 2010/0305604 A1 | 12/2010 | Pah |
| 2010/0312268 A1 | 12/2010 | Belson |
| 2010/0324589 A1 | 12/2010 | Carpenter et al. |
| 2011/0295304 A1 | 12/2011 | Jonsson |
| 2012/0041469 A1 | 2/2012 | Fischell et al. |
| 2012/0165860 A1 | 6/2012 | Shimon et al. |
| 2012/0330342 A1 | 12/2012 | Jone |
| 2013/0096606 A1 | 4/2013 | Bruchman et al. |
| 2013/0131714 A1 | 5/2013 | Wang et al. |
| 2013/0138201 A1 | 5/2013 | Ginn |
| 2013/0178891 A1 | 7/2013 | Russell et al. |
| 2013/0184810 A1 | 7/2013 | Hall et al. |
| 2013/0190856 A1 | 7/2013 | von Oepen et al. |
| 2013/0226223 A1 | 8/2013 | Spenser |
| 2014/0005540 A1 | 1/2014 | Merhi |
| 2014/0031857 A1 | 1/2014 | Richardson |
| 2014/0052170 A1 | 2/2014 | Heuser et al. |
| 2014/0074147 A1 | 3/2014 | Marchena |
| 2014/0074148 A1 | 3/2014 | Glenn et al. |
| 2014/0074152 A1 | 3/2014 | Shezifi et al. |
| 2014/0100597 A1 | 4/2014 | Wang et al. |
| 2014/0155929 A1 | 6/2014 | Belson |
| 2014/0172006 A1 | 6/2014 | Stack et al. |
| 2014/0194920 A1 | 7/2014 | Krahbichler |
| 2014/0214069 A1 | 7/2014 | Franklin |
| 2014/0243881 A1 | 8/2014 | Lees et al. |
| 2014/0249566 A1 | 9/2014 | Quinn et al. |
| 2014/0249567 A1 | 9/2014 | Adams et al. |
| 2014/0249568 A1 | 9/2014 | Adams et al. |
| 2014/0257362 A1 | 9/2014 | Eidenschink |
| 2014/0257366 A1 | 9/2014 | Jonsson |
| 2014/0257367 A1 | 9/2014 | Jonsson |
| 2014/0257368 A1 | 9/2014 | Jonsson |
| 2014/0303667 A1 | 10/2014 | Cox et al. |
| 2014/0330305 A1 | 11/2014 | Rood et al. |
| 2014/0336690 A1 | 11/2014 | Zhadkevich |
| 2014/0336695 A1 | 11/2014 | Naor et al. |
| 2014/0371783 A1 | 12/2014 | Shu et al. |
| 2015/0039016 A1 | 2/2015 | Naor et al. |
| 2015/0066075 A1 | 3/2015 | Russell et al. |
| 2015/0202038 A1 | 7/2015 | Krahbichler |
| 2015/0223920 A1 | 8/2015 | Bruchman et al. |
| 2015/0272732 A1 | 10/2015 | Tilson et al. |
| 2015/0313701 A1 | 11/2015 | Krahbichler |
| 2015/0320540 A1 | 11/2015 | Belson |
| 2015/0351895 A1 | 12/2015 | Eidenschink et al. |
| 2016/0100928 A1 | 4/2016 | Lees et al. |
| 2016/0106531 A1 | 4/2016 | Shezifi |
| 2016/0120636 A1 | 5/2016 | Gera et al. |
| 2016/0151141 A1 | 6/2016 | Zimmerman |
| 2016/0151145 A1 | 6/2016 | Golan |
| 2016/0158506 A1 | 6/2016 | Eliasen et al. |
| 2016/0235515 A1 | 8/2016 | Merhi |
| 2016/0262864 A1 | 9/2016 | Von Mangoldt |
| 2016/0302909 A1 | 10/2016 | Kelly |
| 2016/0317277 A1 | 11/2016 | Carpenter et al. |
| 2016/0317288 A1 | 11/2016 | Rogers et al. |
| 2016/0324621 A1 | 11/2016 | Shezifi et al. |
| 2016/0338828 A1 | 11/2016 | Ginn |
| 2017/0014232 A1 | 1/2017 | Ginn et al. |
| 2017/0035431 A1 | 2/2017 | Zhadevich |
| 2017/0042659 A1 | 2/2017 | Russell et al. |
| 2017/0100144 A1 | 4/2017 | Zhadkevich |
| 2017/0112513 A1 | 4/2017 | Marchand et al. |
| 2017/0112609 A1 | 4/2017 | Purcell et al. |
| 2017/0119518 A1 | 5/2017 | Krahbichler |
| 2017/0165457 A1 | 6/2017 | Zhadkevich |
| 2017/0181835 A1 | 6/2017 | Kleshinski et al. |
| 2017/0189160 A1 | 7/2017 | Krahbichler |
| 2017/0216010 A1 | 8/2017 | Belson |
| 2017/0224462 A1 | 8/2017 | Shimon |
| 2017/0245864 A1* | 8/2017 | Franano ............ A61B 17/12113 |
| 2018/0147041 A1* | 5/2018 | Chouinard ............ A61F 2/013 |
| 2018/0161185 A1 | 6/2018 | Kresslein et al. |
| 2019/0000604 A1 | 1/2019 | Eli |
| 2019/0142566 A1 | 5/2019 | Lansky et al. |
| 2020/0306026 A1 | 10/2020 | Yamanouchi |
| 2021/0007837 A1 | 1/2021 | Haldis et al. |
| 2021/0052375 A1 | 2/2021 | Jones et al. |
| 2023/0000611 A1 | 1/2023 | Fraysse et al. |

FOREIGN PATENT DOCUMENTS

| | | |
|---|---|---|
| EP | 0 923 344 | 2/2005 |
| EP | 1 117 344 | 6/2006 |
| EP | 1 117 343 | 10/2006 |
| EP | 1 389 959 | 11/2007 |
| EP | 1 001 709 | 1/2008 |
| EP | 1 041 940 | 2/2008 |
| EP | 1 435 876 | 12/2008 |
| EP | 1 400 257 | 1/2009 |
| EP | 1 479 357 | 5/2009 |
| EP | 1 613 239 | 6/2010 |
| EP | 0 975 384 | 9/2010 |
| EP | 1 487 526 | 9/2010 |
| EP | 1 905 365 | 10/2010 |
| EP | 1 075 218 | 1/2011 |
| EP | 1 620 037 | 1/2011 |
| EP | 1 583 485 | 9/2011 |
| EP | 2 089 070 | 4/2012 |
| EP | 2 057 967 | 1/2013 |
| EP | 1 706 063 | 10/2013 |
| EP | 1 895 935 | 4/2014 |
| EP | 2 713 944 | 4/2014 |
| EP | 2 779 911 | 4/2017 |
| EP | 2 800 602 | 8/2017 |
| EP | 2 661 305 | 6/2018 |
| EP | 2 385 856 | 6/2019 |
| EP | 1 701 668 | 8/2019 |
| EP | 3 193 778 | 5/2020 |
| EP | 2 654 617 | 6/2020 |
| EP | 3 544 545 | 12/2020 |
| EP | 3 551 128 | 12/2020 |
| EP | 3 586 793 | 6/2021 |
| EP | 2 996 581 | 9/2021 |
| EP | 3 346 949 | 5/2022 |
| WO | WO 2016/011267 | 1/2016 |
| WO | WO-2019183569 A1 * | 9/2019 ............ A61F 2/011 |
| WO | WO 2021/034358 | 2/2021 |

OTHER PUBLICATIONS

International Search Report for International Application No. PCT/US2021/46152, dated Jan. 25, 2022.
https://trisaluslifesci.com/; retrieved Nov. 3, 2022; 8 pages.
https://trinavinfusion.com/; retrieved Nov. 3, 2022; 9 pages.

* cited by examiner

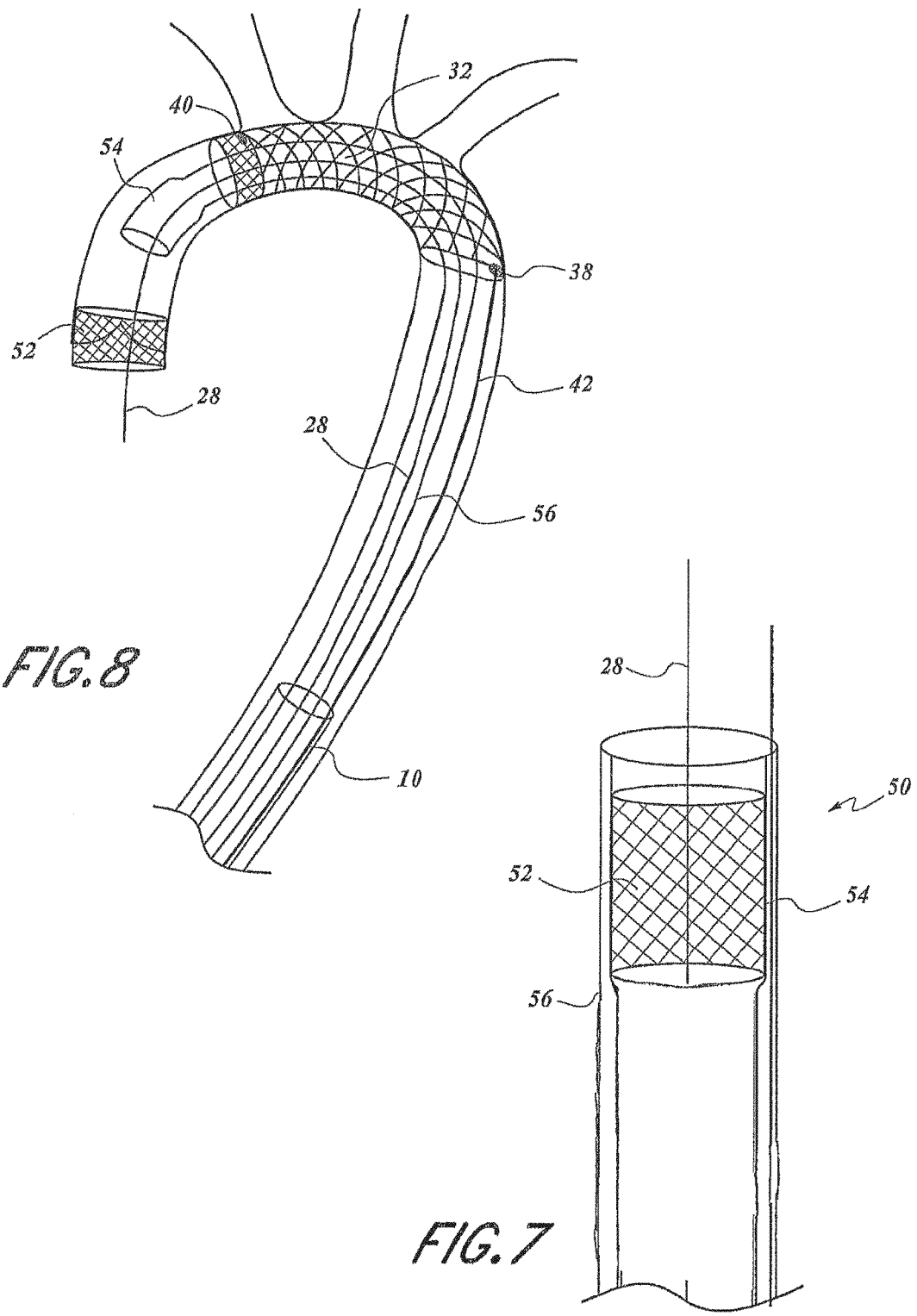

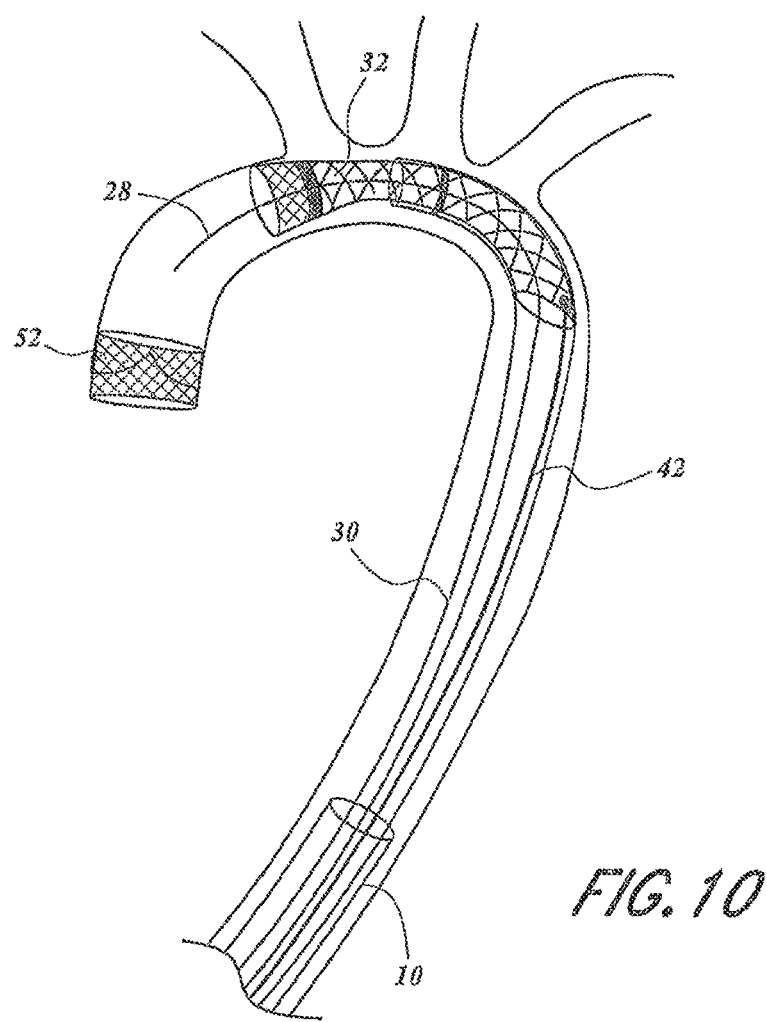

EMBOLIC PROTECTION AND ACCESS SYSTEM

CROSS-REFERENCE TO RELATED APPLICATIONS

This application is a continuation-in-part of U.S. application Ser. No. 16/868,076, filed May 6, 2020, which claims the priority benefit under 35 U.S.C. § 119(e) of U.S. Provisional Application No. 62/888,897, filed Aug. 19, 2019, the entireties of which is hereby incorporated by reference herein.

BACKGROUND OF THE INVENTION

Field of the Invention

The present invention relates to protection of one or more side branch vessels from a parent vessel, such as for protection of the cerebral vasculature during a surgical or interventional procedure of the type that might dislodge embolic debris.

Description of the Related Art

There are four arteries that carry oxygenated blood to the brain, i.e., the right and left vertebral arteries, and the right and left common carotid arteries. The right vertebral and right common carotid are both supplied via the brachiocephalic artery. Thus at the aortic arch the cerebral circulation is supplied via the brachiocephalic, the left common carotid and left subclavian arteries (the three great vessels).

Various procedures conducted on the human body, e.g., circulatory support, transcatheter aortic valve replacement (TAVR), aortic valve valvuloplasty, carotid artery stenting, closure of the left atrial appendage, mitral or tricuspid valve annuloplasty, repair or replacement, can cause and/or dislodge materials (whether native or foreign), these dislodged bodies can travel into one or more of the arteries supplying the brain resulting in, inter alia, stroke. Moreover, atheromas along and within the aorta and aortic arch can be dislodged as the TAVR catheter is advanced toward the diseased aortic valve and subsequently withdrawn after implantation is completed. In addition, pieces of the catheter itself can be stripped away during delivery and implantation. These various forms of vascular debris, whether native or foreign, can then travel into one or more cerebral arteries, embolize and cause, inter alia, a stroke or strokes.

Intraoperative embolic stroke is one of the most significant complications of cardiac, aortic and vascular procedures, diagnosed in 1-22% of patients undergoing cardiovascular surgery. Even more frequently, in up to 70% of cases, patients undergoing heart, valve, coronary artery bypass and aortic surgery experience subclinical embolic events as recorded by transcranial Doppler and MM. Recent data showed an astounding incidence of stroke as detected by MRI in practically all groups of cardiac patients: in TAVR v—84%, Aortic Valve Replacement—52%, emergent coronary intervention—49%, Balloon Aortic Valvuloplasty—40%, Cardiac Ablation 38% and Coronary Artery Bypass Surgery—20%. Debris have reportedly been captured in as much as 98% of cased using certain embolic protection filters. These embolic events lead to cognitive impairment and disability and have a significant impact on patients' recovery.

The main sources of cerebral emboli and stroke in this setting resides in the heart, heart valves, thoracic aorta, and great vessels when these structures are invaded. Even simple cardiac catheterization with an endovascular catheter can induce trauma of the atherosclerotic thoracic aorta leading to formation of embolic particles with subsequent embolic brain injury ranging from latent ischemic foci to a massive or even fatal stroke.

A variety of devices have been proposed that attempt to prevent embolization of the carotid arteries during endovascular and cardiac interventions. These anti-embolic devices, however, have not received wide acceptance due to their complexity and invasive character with the risk of additional trauma to the inner vessel wall resulting in a high risk to benefit ratio. Known devices require insertion of additional hardware into the arterial system or aorta, a procedure that is known by itself to be associated with all classical risks of endovascular intervention, and also multiple catheters risk mechanical entanglement or additional remote vascular access sites. Many devices require increased anticoagulation, which leads to increased risk of bleeding including hemorrhagic stroke.

Thus, there remains a need for an effective cerebral protection device which allows the use of less anticoagulents, effectively blocks embolic debris while permitting optimal perfusion during or following a procedure in the heart.

SUMMARY OF THE INVENTION

There is provided in accordance with one aspect of the present invention, a method of protecting the cerebral vascular circulation from embolic debris released during an index procedure. The method comprises providing an embolic protection delivery catheter having a tubular embolic protection filter in a reduced profile configuration, the filter having a self expandable wire frame, a filter membrane carried by the frame. The embolic protection delivery catheter is advanced through an access sheath to deploy the filter spanning at least one and preferably all three Great vessels of the aortic arch. An index procedure catheter is thereafter advanced through the same access sheath to conduct the index procedure. The index procedure may comprise a TAVR.

In accordance with another aspect of the invention, there is provided an intravascular filter for blocking passage of selected sizes of debris into the cerebral circulation. The filter comprises a self expandable tubular wire frame, having a proximal end, a distal end and a tubular sidewall defining a central lumen.

A porous membrane is carried by the sidewall, the membrane having a distribution of pore sizes. A first group of pores has pores with a maximum dimension of no more than a first threshold such as about 25 microns. A second, smaller group of pores has pores with a maximum dimension of a second threshold such as at least about 50 microns. The prevalence of pores in the first group is at least three times the prevalence of pores in the second group when the tubular wire frame is in an unconstrained, expanded configuration.

In some implementations, the second group of pores will block particles greater than about 120 microns, or greater than about 100 microns, or greater than about 80 microns depending upon desired clinical performance. The prevalence of pores in the first group may be at least about four times the prevalence of pores in the second group.

The sum of the area of all of the pores in all groups is at least about 30% of the surface area of the membrane, and in some implementations the sum of the area of all of the pores is at least about 35% or 40% of the surface area of the membrane when the filter is in an unconstrained expansion. The pressure drop across the filter between the aorta and the great vessels is less than about 10 mm Hg, and in some implementations less than about 5 mm Hg or 2 mm Hg at physiologic flow rates.

The wire frame configuration and thin, flexible membrane of the present invention enable the treatment of a wide variety of diameter aortas and variable anatomy with a single device. The filter has a working range over aorta diameters of from about 20 mm to about 40 mm or more without degradation of filtering efficiency, including conforming to the wall of tapered aortas with a significant change in diameter over the length of the filter. The filter can bend around twists and turns of the aorta, while maintaining contact with the vessel wall. The filter can cover and conform to diseased portions of the wall, without the need to cross the ostia into the great vessels leading to the brain. In addition, the complete tubular configuration eliminates any need to control rotational orientation of the deployment system. In addition, the 360 degree coverage allows treatment of all patients regardless of the launch angles of the great vessels off of the aorta, which can vary circumferentially around the aorta as much as 15 or 20 degrees.

BRIEF DESCRIPTION OF THE DRAWINGS

FIG. 7 illustrates a trans catheter aortic valve replacement catheter.

FIG. 8 illustrates the trans catheter aortic valve replacement catheter deploying an aortic valve through the embolic protection access sheath of the present invention.

FIG. 10 illustrates retrieval of the embolic projection access system filter.

DETAILED DESCRIPTION OF THE PREFERRED EMBODIMENT

The protective filter of the present invention is designed to provide vascular protection and filtering of debris that can be created during interventional procedures. In one exemplary use, the filter will protect the aortic arch during the passage of interventional devices whose destination is the heart. The protective filter will preferably cover all three great vessels (brachiocephalic, left common carotid and left subclavian blood vessels) leading to the brain. The filter includes a pore size distribution that significantly reduces both the size and cumulative volume of debris that would otherwise go to an end organ like the brain thereby protecting against a stroke and other negative impact to cognitive functions.

The device of the present invention is configured to block debris above one or more predetermined threshold sizes from entering the cerebral circulation. Some blocked debris may become entrapped in the membrane, while other blocked debris will be deflected and travel downstream through the aorta. The shorthand term 'filter' is intended to refer to the membrane disclosed herein which has both filtration functions and deflection functions. Terms like debris and particles are used interchangeably herein and are not intended to convey separate meanings.

Trans-catheter Aortic Valve Replacement (TAVR) for example, is a popular and growing interventional cath lab catheter procedure that creates debris capable of causing a stroke, or other cerebral complications. Although embolic protection systems have been proposed in the past, such systems generally require an additional vascular access point and/or additional catheter exchange steps. The protective sheath of the present intention does not require a separate vascular access site.

Vascular access via the femoral artery can be accomplished, for example, using a Perclose ProGlide system (Abbott Vascular) as is understood in the art. This places one or two sutures in the femoral artery at the start of the procedure. These can be used to close 14 F or larger puncture sites in the groin at the end of the procedure. A hollow needle is first introduced from the groin into the femoral artery. A guidewire is introduced through the needle and into the blood vessel. The needle is withdrawn and a blunt cannula with a larger outside sheath is placed over the wire and advanced into the artery. The blunt cannula can then be withdrawn, leaving the access sheath positioned typically in the descending aorta, above the renal arteries, where it is available for various procedural catheters and guidewires to be introduced and exchanged through the access sheath.

Figure 1:
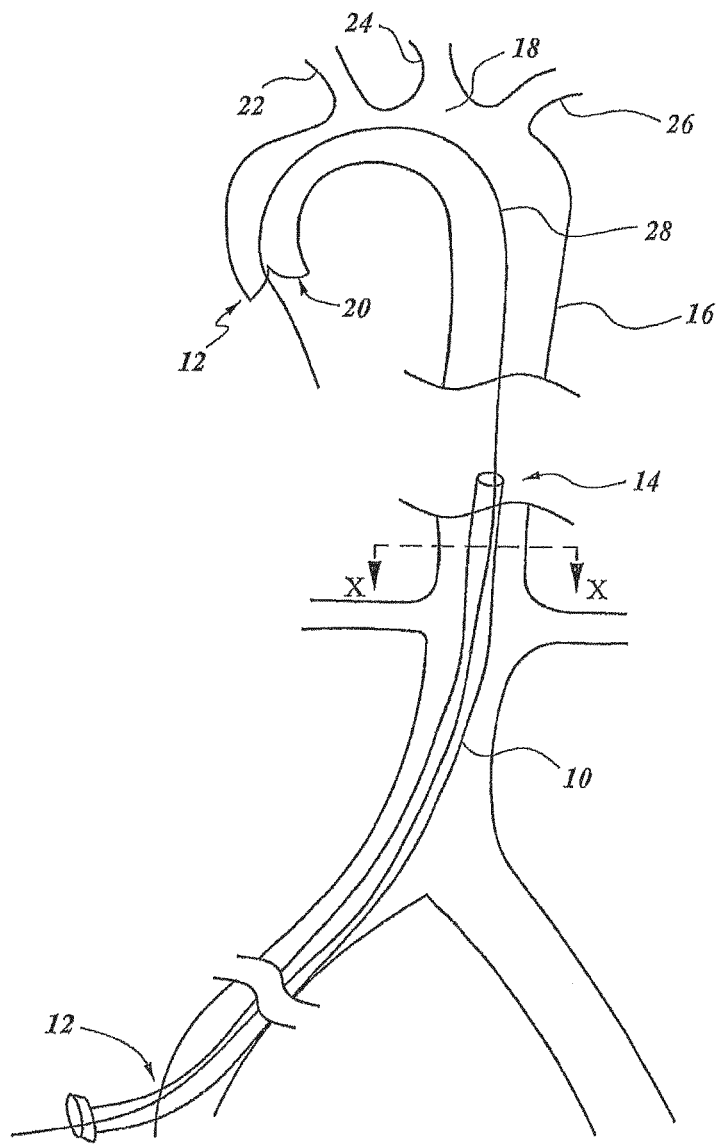
FIG. 1 illustrates an access catheter positioned in the descending aorta with a guide wire extending across the aortic arch and through the aortic valve.

FIG. 1 illustrates an access sheath 10 extending from a femoral artery access point 12 to position a distal end 14 of the access sheath 10 in the descending aortic artery 16 and available to guide a guidewire 28 and procedure catheters superiorly such as to the aortic arch 18 or the aortic valve 20 or beyond into the heart. The initial access needle and blunt cannula have been removed. In the specific procedure described primarily herein, the access sheath is available to guide devices of the present invention to regulate the flow of embolic debris through the ostia of the brachiocephalic artery 22, the left common carotid artery 24 and the left subclavian artery 26 thereby protecting the cerebral circulation. The same access sheath 10 is then used to subsequently guide the index procedure catheter, such as a TAVR delivery catheter.

Figure 2X:
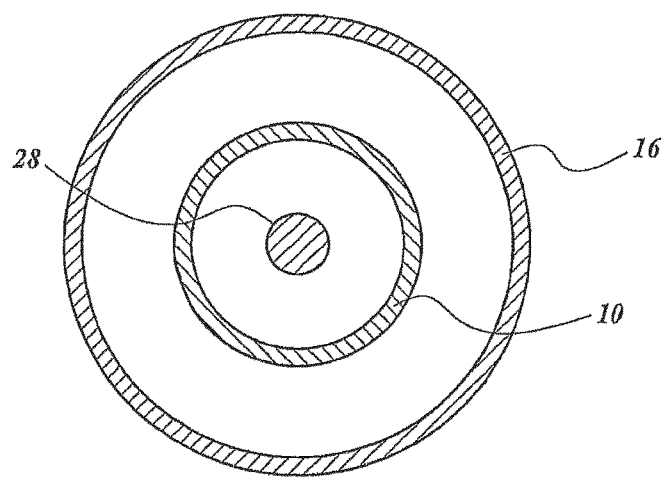
FIG. 2X is a cross-section taken along the lines X-X in FIG. 1.

A suprarenal cross section through the aorta along the lines X-X on FIG. 1 is shown in FIG. 2X, in which the blunt cannula has been removed and a guidewire 28 extends through the TAVR access sheath 10 which may have an ID, for example, of no more than about 28 F or 20 F or no more than about 15 F and in one implementation an ID of about 14 F depending primarily upon the size of the TAVR index procedure catheter (TAVR delivery catheter) size.

The guidewire 28, such as an 0.035" guidewire, is advanced through the aorta over the arch 18 through the aortic valve 20 (see FIG. 1), and into the ventricle (not illustrated). Preferably an exchange length (e.g., 300 cm or longer) guidewire is used to facilitate catheter exchanges in an OTW configuration. A guidewire of about 260 cm or less can be used in a rapid exchange configuration.

The 14 French ID TAVR procedural sheath 10 (18.5 F outside diameter, 22 F expanded outside diameter) is advanced over the 0.035" guidewire beyond the renal arteries and into the descending aorta 16. The Edwards E-Sheath is expandable, while the sheaths used for BSC and Medtronic TAVR systems are not expandable and are sized to accommodate their respective delivery systems. The sheath 10 does not need to expand to accommodate the catheter 30 on accordance with the present invention. This procedure sheath 10 is the same sheath that provides access for the catheter 30 of the embolic protection system of the present invention.

Figure 3:
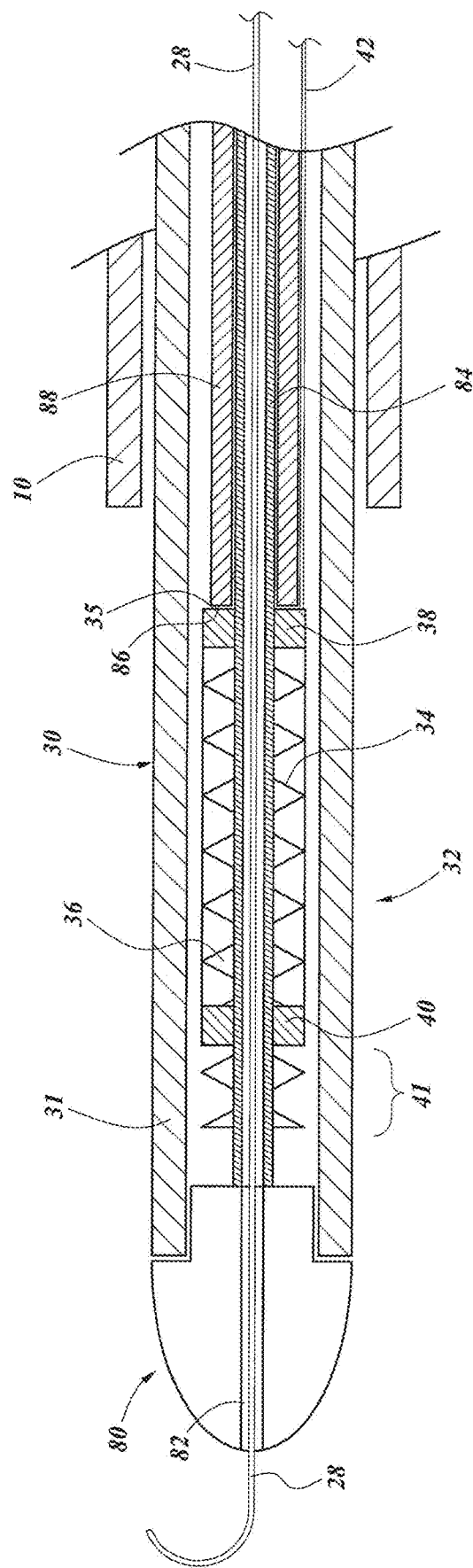
FIG. 3 is a side elevational schematic cross-section through the distal end of an embolic protection access system.

Referring to FIG. 3, there is illustrated an embolic protection delivery catheter 30 having, for example, a less than 14 F OD (e.g., a 13.5 F) tubular body 31, advanced through the 14 F TAVR delivery sheath 10. The delivery catheter 30 may have an ID between about 11 F and 12 F and in one implementation about 11.92 F, and may include a lubricious coating such as a PTFE inner liner. The frame and filter are back loaded into the distal end of the delivery catheter 30 prior to advancing the catheter 30 over the guidewire 28 and through the access sheath 10. The delivery catheter 30 is thereafter axially advanceable beyond the distal end of the 14 F delivery sheath 10. The ID of the delivery sheath 10 preferably exceeds the OD of the catheter 30 by no more than about 0.030 inches or 0.028 inches or less.

Delivery catheter 30 additionally comprises a distal nose cap 80 axially distally displaceable from the distal end of the tubular side wall 31 of catheter 30. Distal nose cap 80 includes an atraumatic distal tip, and a central lumen 82 for movably receiving guide wire 28. Nose cap 80 is carried by an inner support tube 84 which extends proximally to a distal end face 86 of a push tube 88 which extends to a push tube control on or associated with the proximal manifold (not illustrated). Tubular support tube 84 includes a central lumen 82, for slidably receiving guide wire 28 there through. The OD of inner support tube 84 is less than the OD of pusher tube 88, creating an annular distal end face 86 to prevent proximal movement of the expandable frame 34. Proximal retraction of the tubular body 31 of catheter 30 with respect to the pusher 88 exposes the filter 32 which can radially expand into position across the aortic arch.

The pusher assembly of the push tube 88 and support tube 84 may have a flexible tapered tip 80 at its distal end (~105 cm tip to hemostatic valve plus about 30 cm for the proximal handle) for tracking the guidewire and providing a smooth transition through the delivery catheter. The tip may have a radiopaque marker to allow the user to determine its location in the anatomy.

An optional two part handle that has an outer portion attached to the delivery catheter 30 hemostatic valve and an inner portion connected to the inner push tube 88 will allow for grasping and positionally fixing the handle and thus the inner push tube 88, while the outer delivery catheter 30 can travel freely through the procedural sheath, thus deploying, or re-capturing the filter and frame at the distal end of the system.

A hemostatic seal may be provided at the proximal end of the catheter to allow movement of the push tube 88 and filter control 42 wire through the internal lumen of the delivery system, while providing for minimal blood loss through the annular space between the ID of the catheter and the inner push tube, with the filter wire in place.

A one or two or preferably three vessel filter 32 is positioned in a collapsed configuration within the 13.5 or 13.9 F delivery catheter 30. The filter 32 comprises an expandable frame 34 which carries a filter membrane 36 over at least a portion thereof. See also FIG. 11. In the illustrated embodiment, the filter membrane 36 is carried by the frame 34 from a proximal marker 38 to a distal marker 40 which mark the ends of the filtering zone. Additional markers may be desirable to mark the ends of the frame (such as the distal end which extends beyond the filter membrane) in the event that the frame struts are not easily seen under fluoroscopic imaging. The frame distally of the distal marker 40 is an uncovered landing zone 41 with bare metal struts or may have a coating on the wire struts but has open sidewall windows between adjacent struts without the membrane 36.

The membrane 36 may be configured to block the passage of debris as small as 0.5 mm and greater, or 0.25 mm and greater, or 0.1 mm and greater or less. The membrane may be formed by an electrospinning process. Electrospinning refers generally to processes involving the expulsion of flowable material from one or more orifices, and the material forming fibers are subsequently deposited on a collector. Examples of flowable materials include dispersions, solutions, suspensions, liquids, molten or semi-molten material, and other fluid or semi-fluid materials. In some instances, the rotational spinning processes are completed in the absence of an electric field. For example, electrospinning can include loading a polymer solution or dispersion, including any of the cover materials described herein, into a cup or spinneret configured with one or more orifices on the outside circumference of the spinneret. The spinneret is then rotated (or the wire frame rotated near a fixed spinneret), causing (through a combination of centrifugal and hydrostatic forces, for example) the flowable material to be expelled from the orifices. The material may then form a "jet" or "stream" extending from the orifice, with drag forces tending to cause the stream of material to elongate into a small diameter fiber. The fibers may then be deposited on the wire frame. Through a series of passes of the spinneret axially relative to the frame, the fibers can be 'layered' along the frame effectively successively reducing the average pore sizes formed between adjacent fibers. Further information regarding electrospinning can be found in U.S. Publication No. 2013/0190856, filed Mar. 13, 2013, and U.S. Publication No. 2013/0184810, filed Jan. 15, 2013, which are hereby incorporated by reference in their entirety.

A control wire 42 extends from the frame 34 proximally to a filter control on the proximal end of the catheter. Proximal motion of the tubular body 31 relative to the control wire 42 and pusher 88 will retract the tubular body 31 to uncover the three vessel filter 32 leaving it unconstrained. This allows the frame 34 to self expand into, for example, a tubular configuration, having a diameter of at least about 20 mm or 25 mm to about 30 mm or 35 mm or more, and to support the membrane 36 against the wall of the aorta spanning the aortic arch and covering the three great vessels. Thus, the device can be deployed through 14 F access sheath 10, and have a sufficiently large expansion ratio to provide an operating range of vessels having a diameter of from about 20 mm to about 35 mm. The unconstrained transverse cross sectional configuration through the filter zone can be a full circle, or less than a full annular side wall, such as an arcuate configuration extending no more than about 270° or 180° or less but having an arc length sufficient to span the ostia of the great vessels.

The filter 32 may be loaded into a collapsed configuration within the 13.5 F delivery catheter 30 by back loading the control wire 42 through the distal tip of the 13.5 F delivery catheter 30. The control wire 42 is proximally retracted, pulling the covered frame 34 into the tip of the delivery catheter 30. One or two or more ramped struts 35 or a purse string loop (discussed below) may be utilized to facilitate entry of the filter into the distal end of the delivery catheter 30. The 13.5 F delivery catheter 30 may then be loaded over the 0.035" guidewire, into the 14 F ID sheath 10 and advanced distally into the blood vessel.

Figure 4:
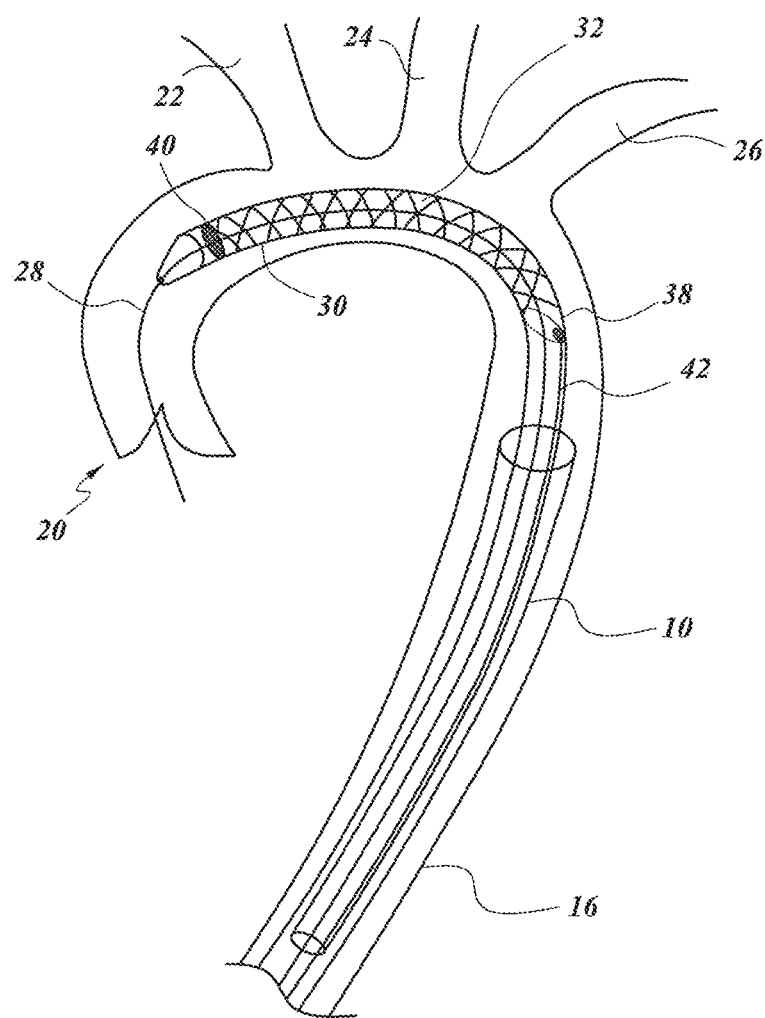
FIG. 4 is a schematic view of the embolic protection system constrained within a deployment catheter and positioned across the aortic arch.
Figure 5X:
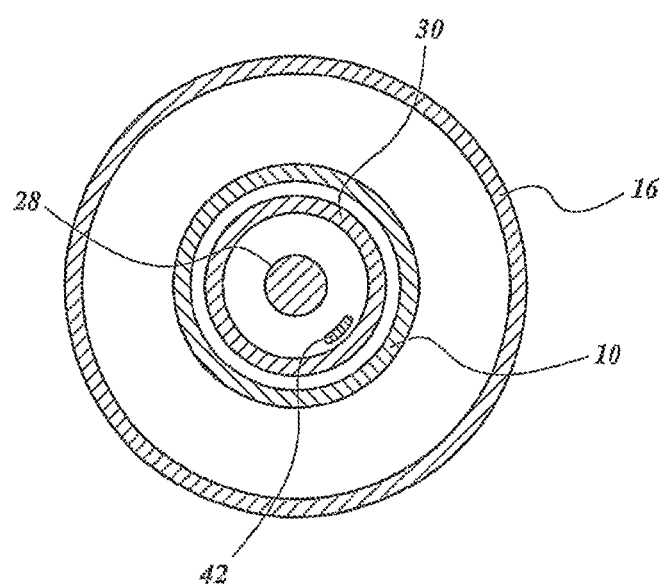
FIG. 5X is a cross-sectional view taken along the lines X-X of FIG. 1, at the procedural stage illustrated in FIG. 4.

Referring to FIG. 4, the 13.5 F delivery catheter 30 with the covered frame is advanced distally with the collapsed filter 32 inside, until the ostia of the three great vessels are located in between the distal marker 40 and the proximal marker 38. The suprarenal cross section through the aorta along the lines X-X on FIG. 1 is shown in FIG. 5X as it may appear in this stage of the procedure, in which the delivery catheter 30 extends through and beyond guide catheter 10 and contains control wire 42 which leads distally to the three vessel filter positioned in the aortic arch.

Figure 6:
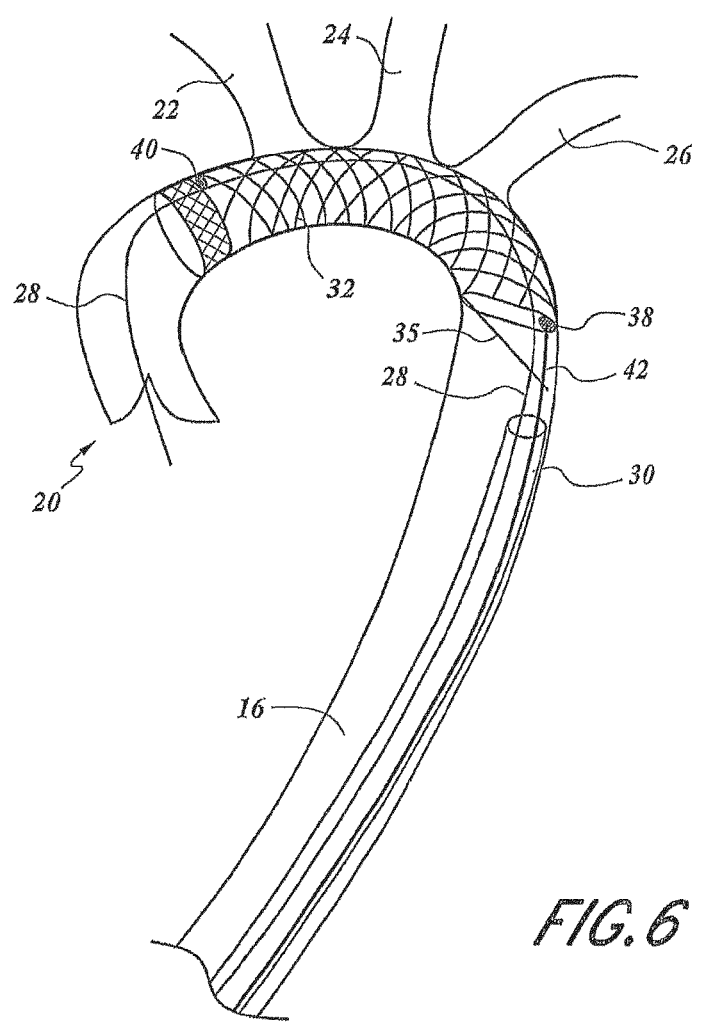
FIG. 6 is a schematic view of the embolic protection access system filter deployed across the aortic arch.

Referring to FIG. 6, once the markers 38 and 40 are confirmed to be on either side of the great vessels covering the aortic arch, the tubular side wall 31 of delivery catheter 30 is proximally retracted relative to the filter 32 to expose the uncovered distal landing zone 41 of the frame 34 so that it might radially expand and engage the wall of the aorta. As the tubular side wall 31 is further retracted to expose the filter 32, the frame 34 will radially expand to cover at least the ostia along the aortic arch. The 13.5 F delivery catheter 30 may then be proximally withdrawn and removed from the patient.

The basic construction of a TAVR delivery system 50 is shown in FIG. 7. A compressed valve and valve support frame 52 is carried within an expandable 14 F ID TAVR procedural delivery catheter 56. A valve pusher 54 is provided to deploy the valve 52. The loaded delivery system 50 is configured to advance over the guidewire 28.

Referring to FIG. 8, the 13.5 F delivery catheter 30 is proximally retracted over the 0.035" guidewire 28 leaving the exchange guidewire 28 in place. The TAVR valve 52 with retention jacket (in a self expandable valve embodiment) and TAVR delivery pusher tube 54 both residing within the TAVR delivery catheter 56 are distally advanced over the 0.035" guidewire to the desired valve (TAVR) deployment location. The TAVR valve is deployed and the TAVR delivery catheter 56 and pusher tube 54 are both withdrawn proximally from the body. In a balloon expandable system, the valve may be crimped down over the balloon and retention jacket may be omitted as is understood in the art.

Figure 9X:
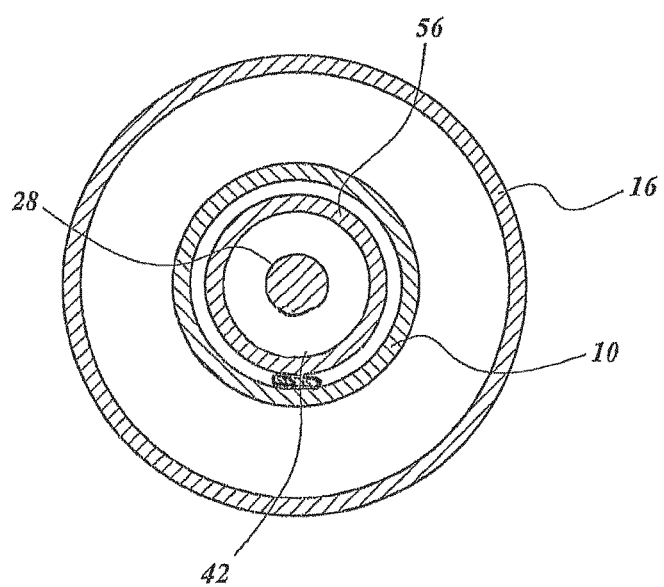
FIG. 9X is a cross-sectional view taken along the lines X-X of FIG. 1, at the procedural stage illustrated in FIG. 8.

FIG. 9X shows the cross-sectional view taken along the line X-X of FIG. 1, at the stage of the procedure illustrated in FIG. 8. The TAVR delivery catheter 56 for delivering the TAVR valve 52 extends axially through and beyond the TAVR procedural sheath 10. The control wire 42 extends axially within the delivery sheath 10 and outside the a TAVR delivery catheter 56.

Thus the delivery catheter 56 has replaced the delivery catheter 30 which has been removed, and the filter remains tethered by the flat control wire 42. Thus, the embolic protection system can be introduced via the same procedural sheath 10 as is the TAVR valve, although it can also be introduced via a separate access site if desired.

The embolic protection system may then be removed in the same procedure, or in a separate, subsequent procedure. Referring to FIG. 10, the 13.5 F delivery catheter 30 is advanced distally back over the 0.035" guidewire and over the control wire 42. The 13.5 F catheter is distally advanced over the filter 32 while proximal traction is maintained on the control wire 42, to capture the covered frame and any trapped debris. The delivery system with recaptured filter may then be proximally retracted with or over the 0.035" guidewire and withdrawn from the patient.

Figure 11:
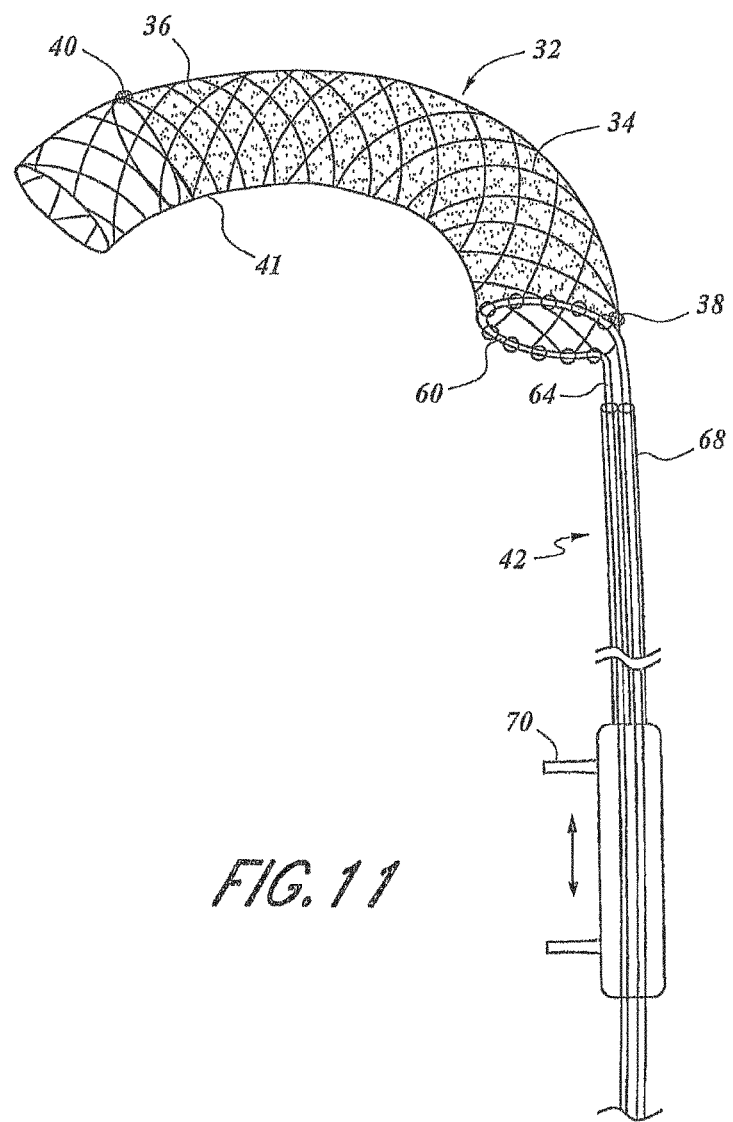
FIG. 11 is a schematic view of an embolic protection access system filter.

Additional details of one embolic protection system of the present invention are shown in FIG. 11. The expandable frame 34 comprises a plurality of filaments joined at a plurality of apexes 60 surrounding the proximal opening to the tubular three vessel filter 32. A suture 62 may be threaded through the apexes 60 into a loop with at least one or two suture tails 64 extending proximally to a proximal manifold or control outside of the patient. Proximal retraction of the suture tail 64 with respect to the expandable frame 34 will cause the proximal opening of the tubular filter 32 to reduce in size, with a 'purse string' tightening effect. In the illustrated embodiment, the suture loops around the proximal opening to the filter, and produces a first suture tail 64 and a second suture tail 66 which extend all the way to the proximal end of the catheter.

The control wire 42 in this implementation is tubular having one or two lumens, and the suture tails 64 and 66 extend proximally through the central lumen or lumens of the control wire 42. Preferably, the tubular control wire 42 is flat (rectangular or oval in transverse cross section) or otherwise provided with a major axis in a circumferential direction that is greater than a minor axis in the radial direction when measured in cross-section. This allows the minimization of the space between the outside diameter of valve delivery catheter 56 and the inside diameter of the access sheath 10, as may be understood in connection with FIG. 9X.

The flat tube may be a tube with 2 lumens side by side and constructed as an extruded polymer, or as two metal tubes brazed or welded together along their length. It could alternatively be a round tube, which has slightly higher profile, depending upon the particular system. A round tube of about 0.030 inch or less will generally not have much negative impact on deploying the valve thru the introducer.

Alternatively, two wires may extend through the deployment catheter using the deployment catheter as the base of the noose to tighten and constrict the proximal end of the stent.

A single relatively large wire greater than about 0.010 inch diameter, may be used within the deployment catheter and be sufficiently controllable when left within the introducer sheath and aorta. Smaller wires (e.g., 0.010 or smaller) preferably extend through support tubes or tube control them and keep from tangling or getting in the way. The smaller wires make cinching the purse string easier due to the bend in small radii needed to close the purse string, but small wires need the support along their length to push out and release the cinch and open the proximal end of the stent.

An alternative is to provide a tube running from the handle to the tubular wire frame 34 which is physically/permanently connected to the proximal end of the frame 34. A single wire has a distal end anchored to the frame adjacent the tube and extends around the circumference and through the braid tips and then passing proximally within the tube to the handle. This enables the pull/push on only a single wire to close/open the purse string.

To retrieve the filter 32 following completion of the index procedure, one or both suture tails 64, 66 are proximally retracted by manipulating a control such as by retraction of a slider switch 70 on the proximal handle. The distal end of the control wire 42 abuts and prevents proximal movement of the frame 34. Retraction of the suture thereby reduces the diameter of the proximal opening on the filter. That, along with the angled proximal face of the frame 34 allows the delivery catheter 30 to be distally advanced relative to the filter, to recapture the filter for removal as illustrated in FIG. 10.

The foregoing discussion has primarily been directed to positioning a filtration device in the aorta to provide cerebral protection during TAVR procedures, where during the catheter based procedure, debris from the atrium, aortic valve, or aorta can be dislodged, travel to the aortic arch 18 and enter the cerebral circulation through the great vessels leading to the brain. However, the devices of the present invention can be utilized in any of a variety of peripheral, coronary or neurovascular environments where filtering or deflecting debris from entering a branch vessel off a parent vessel may be desired.

The cerebral protection system of the present invention may also be utilized during a variety of additional cardiovascular interventions where debris could be generated from the Left Ventricle, Mitral Valve, Left Atrium, Aortic Valve, or Aorta and enter the great vessels (3) to the brain. These include other valvular surgery procedures such as open aortic valve replacement, open mitral valve replacement, open mitral valve repair, trans-catheter mitral Valve Replacement (TMVR), and balloon valvuloplasty. Additional index procedures include, circulatory support such as with the Impella pump, Left Ventricular assist devices, Electro Physiology Ablation (A-Fib), Left Atrial Appendage closure, Atrial Septal Defects (ASD), PFO closure procedures, and other cardiac surgery where bypass is utilized.

Any procedure that is performed with access from the arterial side would allow the embolic protection device and procedure of the present invention to be performed through the procedural access sheath 10. Procedures that require open access, or venous access would require a separate access site.

Details of additional implementations of the invention are described below, with reference to FIGS. 12-14. Any particular details of the following discussion and previous discussion can be interchanged as will be understood by those of skill in the art, depending upon desired clinical performance.

Figure 12:
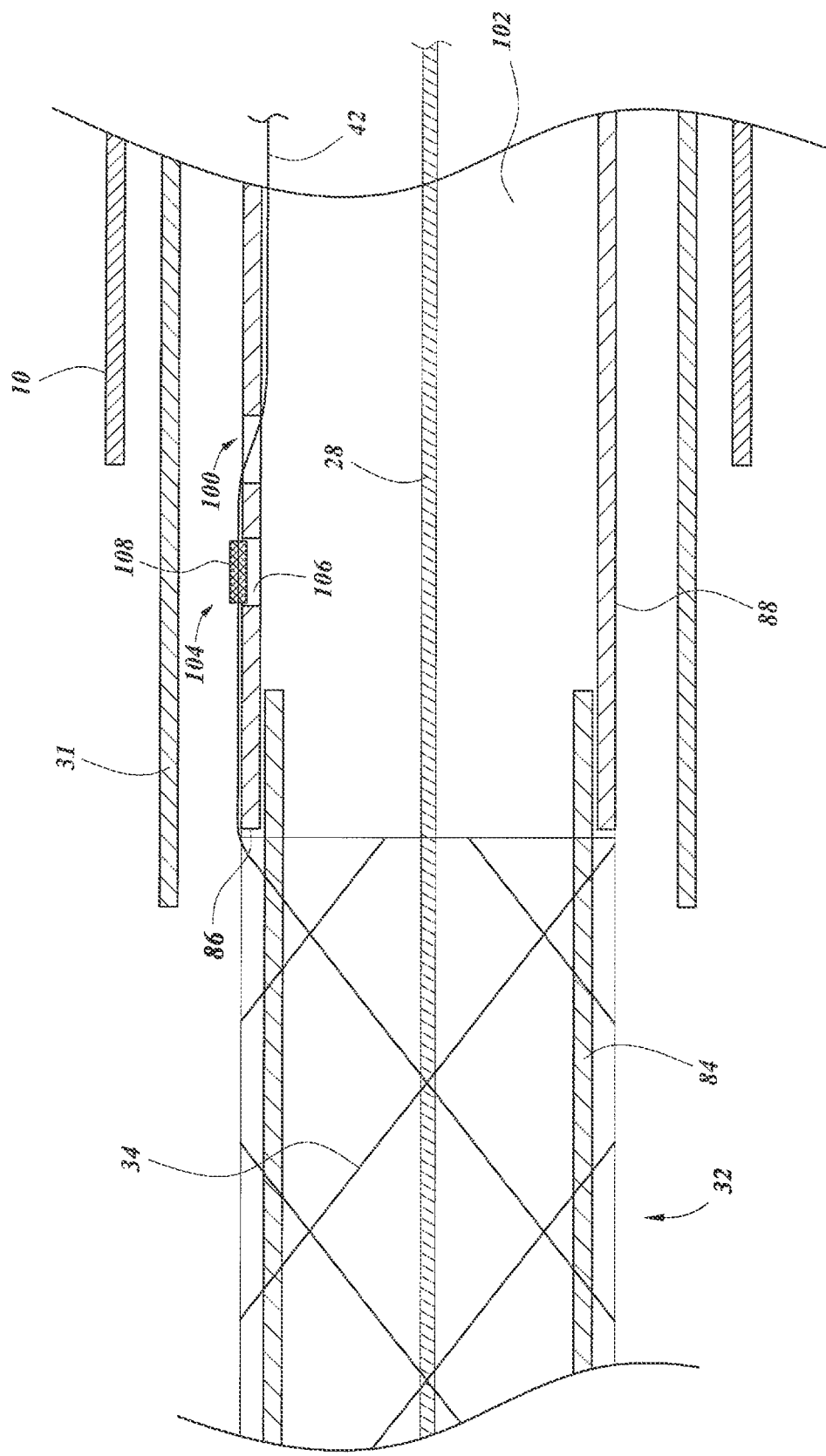
FIG. 12 is a side elevational detail view of a variation of the construction shown in FIG. 3.

FIG. 12 shows a variation on the construction shown previously in FIG. 3. The outer tubular sheath 31 preferably has an outside diameter (OD) of less than 14 F (e.g., in one example about 0.182"). This is less than the internal diameter of the Edwards E-sheath (smallest ID of all of the current TAVR delivery sheaths). The ID of the outer sheath 31 may be about 0.155" (11.92 F), with a liner (PTFE) for low friction release of the filter. The body of the catheter 30 may include a stainless steel braided core for support of the sheath circularity and axial stiffness, with an outer jacket of about 53 Shore D PEBAX. An embedded radiopaque marker between the liner and outer jacket at the distal end of the sheath 31 is used for deployment of the distal end of the filter in the ascending aorta.

The outer sheath 31 with the compressed filter 32 allows the operator the ability to navigate the system over the aortic arch, with sufficient column strength to allow retraction and advancement of the sheath 31 over the compressed frame. The delivery system with the compressed filter yields sufficient softness for tracking over a 0.035" guidewire. With the elongated frame captured in the distal end of the outer sheath 31, the catheter shaft preferably provides adequate axial stiffness (pushability) to deploy and recapture the frame from a fully expanded diameter of as much as about 45 mm without buckling.

Graduated flexibility, or stiffness can be incorporated into the sheath 31 by changing the outer layer of PEBAX to a higher durometer material in the proximal end compared to the distal end or by varying the pitch and/or wire diameter within the braid. This can be accomplished by decreasing the pitch of the braid, substituting thick wires in the proximal end, or making the outer coating from a higher durometer material as will be understood in view of the disclosure herein.

Referring to FIG. 12, the inner push tube 88 may comprise nylon or other polymer having sufficient axial stiffness (column strength) to transmit sufficient support to the collapsed filter 32 during proximal retraction of the tubular sheath 31, and less "compression loading" of the push tube in use. Push tube 88 may alternatively comprise close wound stainless steel springs with coating or heat shrink, or embedded braided tubing. The proximal end of push tube 88 (not illustrated) is bonded to a stainless steel tube that runs through the handle. The stainless steel tube provides axial rigidity in the unsupported portion of the handle.

The push tube 88 ends in a distally facing end face 86, configured to provide a stop surface for the proximal end of the wire frame 34. End face 86 may be located within the range of from about 20 and about 30 cm from the distal end of the catheter 30.

The support tube 84 may be concentrically slip fit into the distal end of the push tube 88 and secured such as by welding, adhesives or other bonding technique depending upon the construction materials. In one implementation, the support tube 84 comprises a secondary nylon tube sized to fit over the primary push tube and take up space within the outer sheath, thus confining the end of the frame and pushing at the proximal end of the frame at the distal weld points.

The control wire 42 extends from the proximal end of the frame 34 proximally along the outside of push tube 88 to a port 100 which allows the control wire 42 to enter the central lumen 102 of push tube 88. Control wire 42 extends proximally through the central lumen 102 to the proximal manifold.

A releasable interlock 104 is provided to lock the frame 34 against relative axial movement with respect to the push tube 88. In the illustrated implementation, a first complementary surface structure such as a recess 106 is provided on the push tube 88. Recess 106 may extend part way or all the way through the side wall of support tube 88. A second complementary surface structure such as an engagement surface on a block 108 is carried by the control wire. The block 108 is configured to engage the recess 106 when the frame is compressed within the tubular body 31. The block 108 may comprise a section of hypotube, a clip, an adhesive or other structure mounted to or formed on the control wire 42, and may be located on the control wire within the range of from about 2 inches to about 4 inches, and in one implementation about 3 inches from the frame 34.

Once the tubular body 31 has been retracted proximally of the interlock 104, the block 108 is able to travel radially outwardly under force supplied by the radially expanding frame 34, disengaging block 108 from the recess 106 and allowing the push tube 88 and support tube 84 to be proximally withdrawn from the wire frame 34, leaving the control wire connected to the deployed frame 34.

Running both the control wire 42 and the guidewire 28 through the inner lumen 102 of the push tube 88 simplifies sealing at the proximal end of the catheter 30 as both will run through a single hemostatic seal. Dimensions for one embodiment of the inner push tube 88/support tube 84 assembly is as follows. Stainless steel tubing at the proximal end of the push tube 88 has a length of about 18 inches and OD of about 0.148 inch. The push tube 88 may have an OD of about 0.125 inch and ID of about 0.078 inch. The support tube 84 has an OD of about 0.050 to provide a reduced OD frame nesting area, an ID of about 0.038 inches and an axial length within the range of from about 8 inches to about 12 inches and in one implementation about 10 inch long.

The OD of the push tube 88 is typically about 0.120 inch diameter to accommodate the collapsed frame's funnel wires and still allow smooth movement within the outer sheath 31. The inner diameter of push tube 88 must accommodate both the 0.035" guidewire and the filter pull wire and allow each to move independently. This would require an ID of at least about 0.052 inch, and may be at least about 0.06 or 0.07 inches and in one implementation is about 0.078 for the inner diameter of the push tube 88. The inner push tube will terminate proximally at the hemostatic valve and handle attachment, where it will transition to a hypo tube that will facilitate the deployment and re-capture function of the handle and delivery catheter 30. At the proximal end of the hypo tube and handle assembly will be a hemostatic valve to seal around the 0.035" guidewire through the length of the device, and filter/frame push/pull wire.

Figure 13:
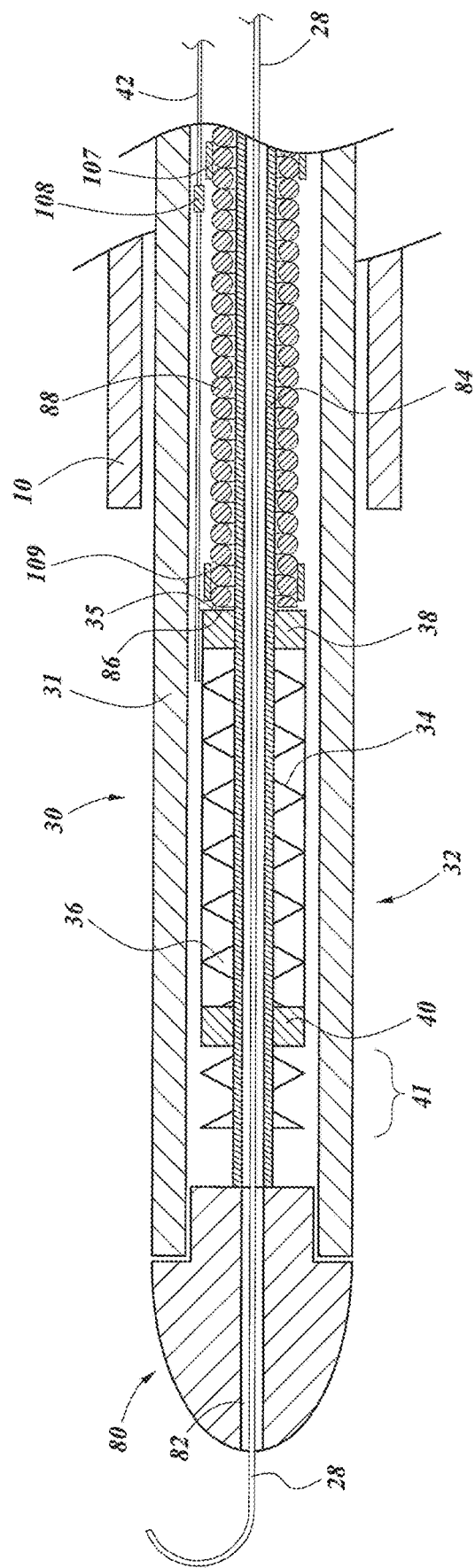
FIG. 13 is a side elevational detail view of a further variation of the construction shown in FIG. 3.

A further modification is shown in FIG. 13. The push tube 88 in this implementation comprises a spring coil which is bottomed out with adjacent filars in close proximity or contact with each other. This provides high column strength while retaining good flexibility. The coil may have an OD of about 0.080 inches and an ID of about 0.060 inches. The control wire 42 extends proximally from the frame 34 on the outside of the spring coil push tube 88, in between the spring coil push tube 88 and the ID of the tubular body 31.

The block 108 is entrapped in the space between the push tube 88, tubular body 31, and a proximal stop 107 and a distal stop 109. Proximal stop 107 and distal stop 109 are engagement structures carried by push tube 88, and in one implementation can be rings concentrically mounted over the push tube 88 and bonded thereto such as by welding, adhesives, compression fit or other attachment technique. Proximal stop 107 and distal stop 109 may be spaced axially apart by a distance within the range of from about 1 cm and about 10 cm.

Figure 14:
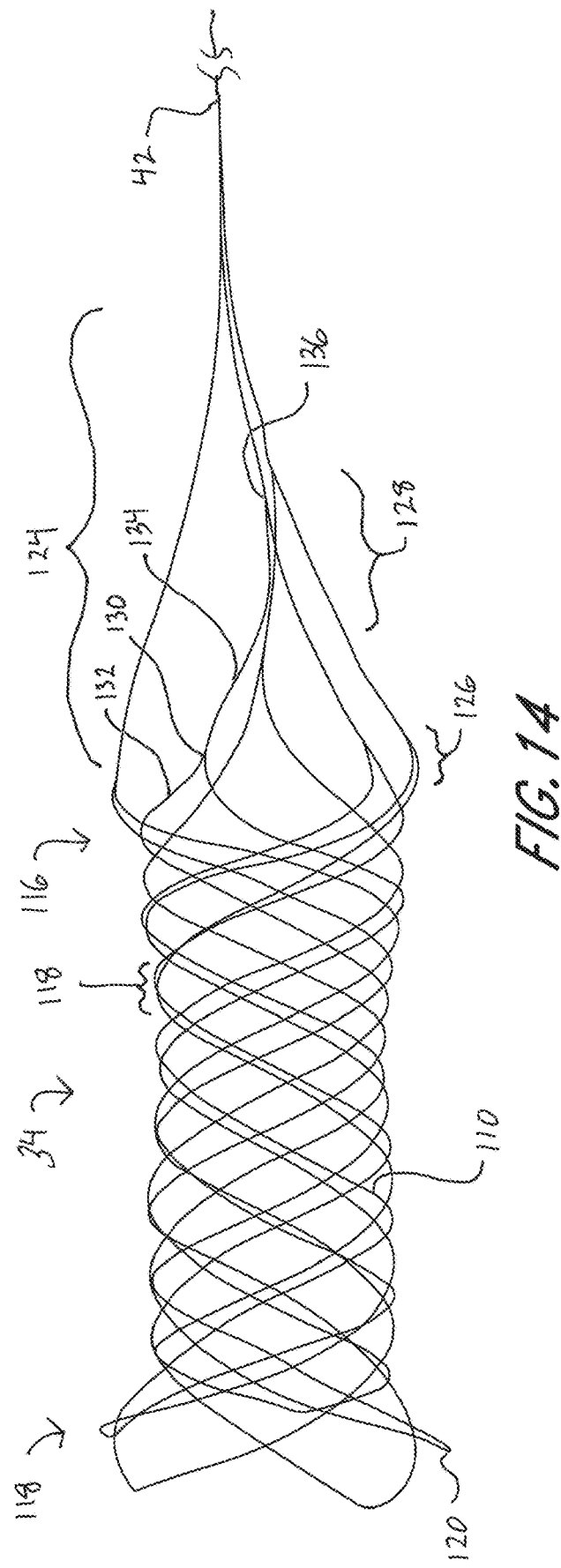
FIG. 14 is a side elevational view of a wire frame for supporting a filter membrane, in an unconstrained expansion state.

Referring to FIG. 14, one implementation of a filter frame 34 is described. The frame 34 is shown in an unconstrained expansion, having a plurality of sidewall wires 110 forming a tubular sidewall 114 extending between a proximal end 116 and a distal end 118. The sidewall 114 may include a series within the range of from about three to about 10 and in one implementation five wires 110 which in one implementation are 0.0155" nitinol wires. The wires 110 may have lengths within the range of from about 15" to about 40", generally within the range of from about 20" to about 35" and in one example are about 27" in length.

Each wire 110 extends helically distally along the sidewall to the distal end 118 where it folds back to form an apex 120 and extends helically proximally so both ends of the wire are in a proximal location on the frame 34. Alternatively, the distal ends of wires can be free ends, or welded to one or more adjacent wire ends.

In the illustrated implementation, the wires 110 are woven over a mandrel with distal loops 120 inclining radially outwardly (bend angle is about 125 degrees) in the landing zone 41 creating a trumpet flare at the distal end 118 having an OD of at least about 35 mm or 40 mm or in one implementation about 45 mm in an unconstrained expansion. A smaller generally cylindrical diameter along the mid section may be no more than about 35 mm or 32 mm. A radially enlarged landing zone 41 at the proximal end 116 may have an OD of at least about 35 mm or at least about 40 mm. Alternatively, the unconstrained expansion may produce a substantially constant diameter throughout the length of the frame, or either the proximal enlargement or the distal enlargement may be used without the other, depending upon the desired performance and intended vessel size.

The larger diameter filter/frame (trumpet) at the distal landing zone 41 may be an advantage of the filter when the landing zone 41 is positioned in the large diameter ascending aorta. This will help create a vessel "seal" at the entry point of the filter. This helps to minimize the risk that debris generated from the procedure in the heart, will enter the great vessels.

The illustrated embodiment produces five distal apexes 120 and ten proximal ends because of the use of five folded wires. The proximal wire ends are off set circumferentially so that they extend proximally from the tubular sidewall all within an arc of no more than about 270 degrees or 220 degrees or less of the circumference of the tubular sidewall.

The proximal end of each wire is connected to an adjacent wire is a series of axially spaced apart junctions distributed over a transition zone 124 that may have an axial length of at least about 1 cm, preferably at least about 2 cm and in some embodiments at least about 2.5 cm or 3 cm. Axially offsetting the welds optimizes the collapsed crossing profile by avoiding welds stacking up in a common transverse plane.

The wires in the transition zone ramp the OD down from the expanded diameter of the proximal end 116 of the frame (e.g., at least about 30 mm or 40 mm) down to a single control wire 42. This is accomplished with a series of wire side welds with a first weld zone 126 to transition from 10 wires down to five. In a second, proximal weld zone 128 wires are transitioned from five down to three and then three down to one resulting in all wires funneling down in a proximal direction into a single (e.g., 0155") control wire 42 that runs the length of the delivery catheter, through the handle and exits proximally at the hemostatic valve.

For example a first weld 130 in the first weld zone 126 joins a proximal end of a first wire 132 to a side of a second wire 134. Five such welds are shown in the first weld zone 126. Second wire 134, for example continues proximally to the second weld zone 128 where an end weld 136 joins it to a third wire 138. Three such wires 138 continue proximally to the control wire 42.

This results in an un-restrained length of about 9 cm for the filter. The actual length in the aorta will be determined by the vessel diameter over the 9 cm length (smaller diameters result in elongation). The length of the frame when retained inside the delivery catheter is about 24.3 cm. The woven wires are spaced about 72 degrees apart on the mandrel and heat set for 20-26 minutes at about 920 degrees (to maintain outside diameter and spacing between the wires).

Each wire 110 makes no more than 10, typically no more than six and in some implementations no more than four complete revolutions about the longitudinal axis of the frame. This results in axial lengthening of at least about 100% (doubling) or 150% or 175% or more in response to radial compression upon loading into the 14 F tubular body 31.

Once the frame is heat set, it is tumbled and electropolished for a rough surface. The frame may then be coated such as by dip coating in polyurethane to form fixed position crossing points where adjacent crossing filaments can pivot about the crossing point but not slide axially along either wire.

The coating of the frame prior to applying the electro spun coating (membrane) holds the wire positions relative to other wires and keeps the wires from sliding relative to one another. This creates a consistent hinge out of each wire crossing point. The coating also provides a better surface for the electro spun coating (membrane) to adhere to compared to the metal frame. Both of these features will add to filter durability. Adding additional electro spun material (more passes of the spinneret) to the proximal and distal end sections of the frame, where the diameter is at its largest (40-45 mm), increases the adherence of the coating (membrane) to the frame. These areas will see the highest stress points to the filter/frame during the procedure.

The coated frame is then loaded on a mandrel and electro spun with a Urethane (Tecothane) dispersion at a shore hardness that yields a cell covering that can expand and contract with frame expansion and contraction. The material is applied to the frame through an electro-spinning process onto the rotating mandrel that results in a covering (membrane) that yields a distribution of different sized openings or pores throughout the length of the filter. Typically the largest of the distribution of openings will have a maximum cross sectional dimension of no more than about 180μ, no more than about 130μ, no more than about 110μ or 100μ or 80μ or less, not counting larger potential statistical outliers that have no meaningful effect on performance.

In addition to pore size distribution, open area, thickness of the covering and membrane flexibility all may effect filter performance.

As the frame is deployed around a curve, a pore on the outer edge elongates in length in the direction of the curve and is compressed perpendicular to the length. This can be up to 50% increase in length while the perpendicular measurement appears to decrease by about 40%.

For a pore on the concave surface of the curve, the change in length along the curve is less obvious, it generally decreases in length about 3% under compression while the perpendicular measurement remains essentially unchanged. As the filter elongates, the porosity and pore size is reduced. Porosity at very small aorta diameters (22 mm diameter) is approximately 0.20 (20 percent).

The filter pore size preferably substantially maintains filter efficiency throughout these range of conditions. As measured by the porosity and observationally of large pore dimensional behavior, the maximum pore size is defined by the coating process at the fully deployed diameter. Elongation of the frame reduces the diameter, porosity and maximum size of particle that will fit thru the pore.

The Filter needs to perform at multiple vessel diameters (22-45 mm) and over the aortic arch which can have multiple radii and three dimensional tortuosity. The covering adds very little to the device profile (0.0005") and minimally affects the flow characteristics to the covered blood vessels. The filter cover appears to be adherent to the frame, durable and not thrombogenic. In testing that we have done, the porosity ranges from 40% at fully deployed diameter of 31.6 mm, down to 25% porosity at 22 mm diameter.

For the effect of decreasing diameter on porosity (% open space), porosity climbs as diameter is increased:

| Frame Diameter | % Open Area |
| --- | --- |
| 32 mm (as built) | 41.8% |
| 28 mm (straight) | 33.0% |
| 24 mm (straight) | 27.8% |
| 20 mm (straight) | 19.7% |

This may be attributable to the pores axially elongating and narrowing circumferentially as diameter goes down.

This pore size distribution creates multiple levels of filtering, created by the multiple pore sizes in the filter (e.g., 80μ and below, 60μ and below, 40μ and below, etc.). This should lead to less total volume of particles passing through the filter to the brain compared to conventional filters which only block particles above a threshold size, but do not reduce the cumulative volume of particles below that threshold from reaching the brain. It is well documented the volume of debris to the brain, correlates to cognitive impairment & stroke. This additional filtering is achieved with no clinically significant reduction on blood flow to the brain, and in some implementations no measurable drop in pressure across the membrane.

Figure 17:
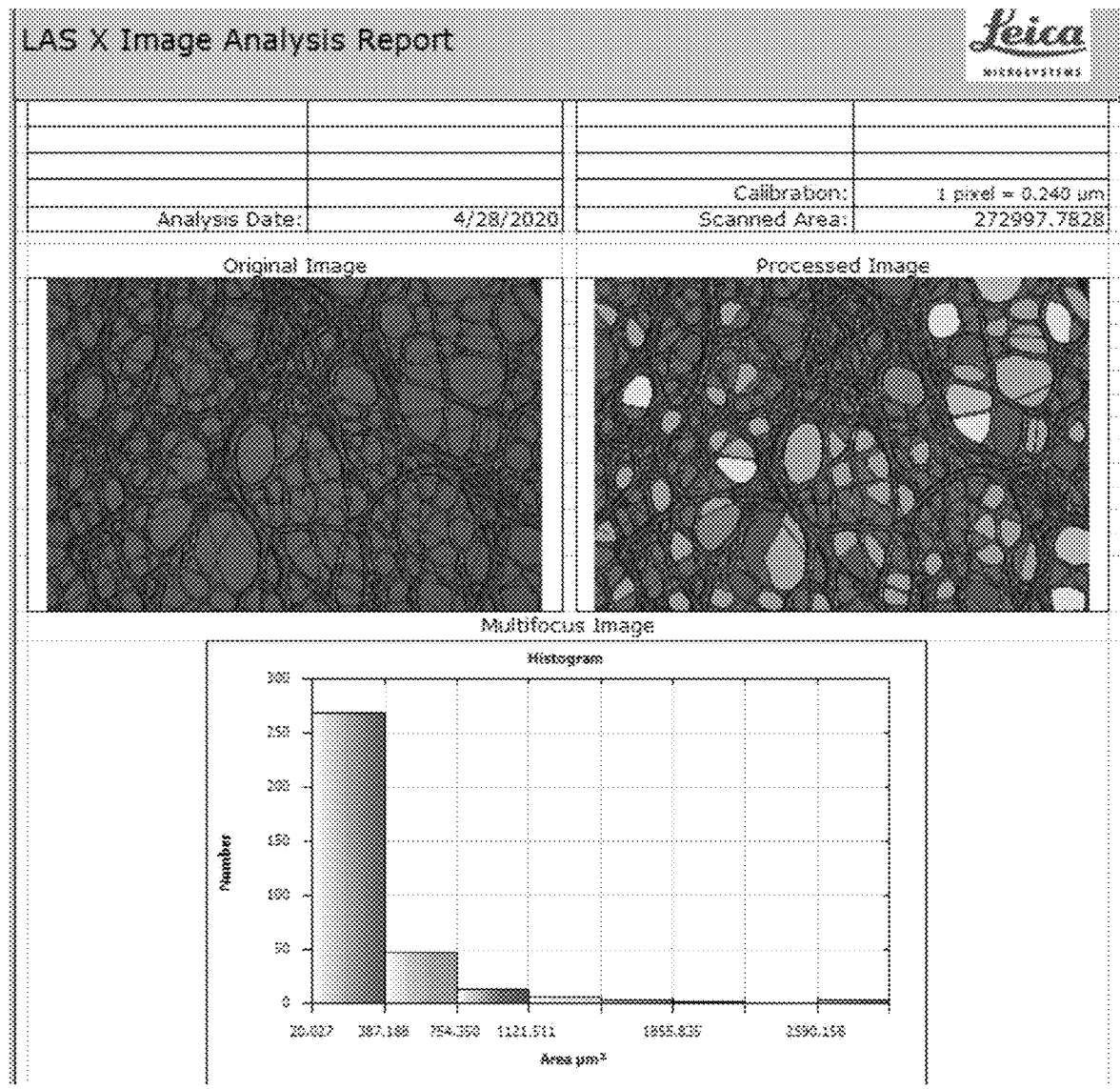
FIG. 17 is a histogram of the distribution of pore sizes in a filter membrane of the present invention.

FIG. 17 is an image and analysis performed with a Leica microscope and Leica image analysis software, to map the pore size distribution. By far the greatest number of pores (first row in the chart) is a first group of pores within the 20-387 square microns size range (equivalent to as large as a 22 micron diameter pore). The next most predominant number of pores is a second group of pores within the 387 to 754 square microns size (31 micron). A third group of pores is within the 754 to 1122 square micron size (38 micron). The largest observed hole is nominally 3000 square microns (equivalent to a 61.8 micron diameter pore). Additional pore distribution data is shown in the table below:

| Bin | Area [μm$^2$] Lower | Area [μm$^2$] Upper | Count | Percent of Total Number |
| --- | --- | --- | --- | --- |
| Bin 1 | 20.027 | 387.188 | 269 | 78.198 |
| Bin 2 | 387.188 | 754.350 | 48 | 13.953 |
| Bin 3 | 754.350 | 1121.511 | 13 | 3.779 |
| Bin 4 | 1121.511 | 1488.673 | 6 | 1.744 |
| Bin 5 | 1488.673 | 1855.835 | 3 | 0.872 |
| Bin 6 | 1855.835 | 2222.996 | 2 | 0.581 |
| Bin 7 | 2222.996 | 2590.158 | 0 | 0.000 |
| Bin 8 | 2590.158 | 2957.319 | 3 | 0.872 |

As the blood and any particles hit the filter, if the particle is smaller than the pore size it happens to encounter, it can pass through the filter. If it is larger than the pore it encounters, it is stopped at the surface of the filter. Arterial flow through the central lumen of the filter will deflect much of the particle mass stopped at the surface of the filter downstream, away from the cerebral vessel, and minimize the risk of the filter becoming occluded and raising a pressure drop across the filter.

In one implementation the filter can thus filter all particles greater than a preset threshold (e.g., 80 microns) but it will also provide some filtration of particles of lower sizes as shown in the histogram of FIG. 17 due to the randomness of particle size and pore size encounters. At a certain pore size (8-10 microns it essentially filters and prevents red blood cells from passing. But the number of pores of that small size are insignificant so essentially all pores allow the passage of blood and the large total open area (sum of all pores) is sufficient for the filter to impose no clinically meaningful pressure drop across the filter.

Friction between the filter frame 34 and the ID of the tubular body 31 is preferably low to facilitate deployment and potential recapture by distal advance of the tubular body 31 back over the frame 34. Generally, retraction of the tubular body may be accomplished under a pulling force of less than about five pounds, preferably less than about 3 pounds or 2.5 pounds or 2 pounds. The open area of the frame 34 (total area of the sidewall less the area of the wire struts) is at least about 80% and generally at least about 85% or 88% and in one five wire embodiment described herein is in excess of 90% (91.5%).

In the implementation of FIG. 14, the frame 34 has an axial length of about 10.2 cm at an expanded diameter of 32 mm (including the trumpet shaped landing zone 41 but not the funnel wires in the transition zone 124). Reducing the OD of the frame 34 to 31.8 mm increases the length to about 13.5 cm (just from compressing the trumpet shaped landing zone 41 down to the OD of the adjacent tubular body). Reducing the OD of the frame to about 28.6 mm increases the length to about 15 cm. Reducing the OD of the frame to about 25 mm increases the length to about 17 cm. Reducing the OD of the frame to about 22 mm increases the length to about 18.2 cm.

Thus a 10 mm expansion of the diameter of the frame produces a foreshortening of at least about 4 cm or 6 cm and in some embodiments at least about 7 cm or 7.5 cm and in one embodiment about 8 cm.

For the frame length, from distal end to the block 108 (see FIGS. 12 and 13) in an unconstrained expansion the length is about 21 cm, so the funnel wires of the transition zone 124 add about 10.8 cm in length. When fully elongated inside the tubular body 31, the length is at least about 28 cm or 30 cm and in one example is about 33 cm.

The embolic filter and delivery system may be supplied in a single sterile package and tray. Once the tray is transferred to the sterile field, the catheter and filter delivery system can be prepared in the tray. Saline will be added to a hydration chamber where the exposed and expanded filter can be hydrated.

Figure 15:
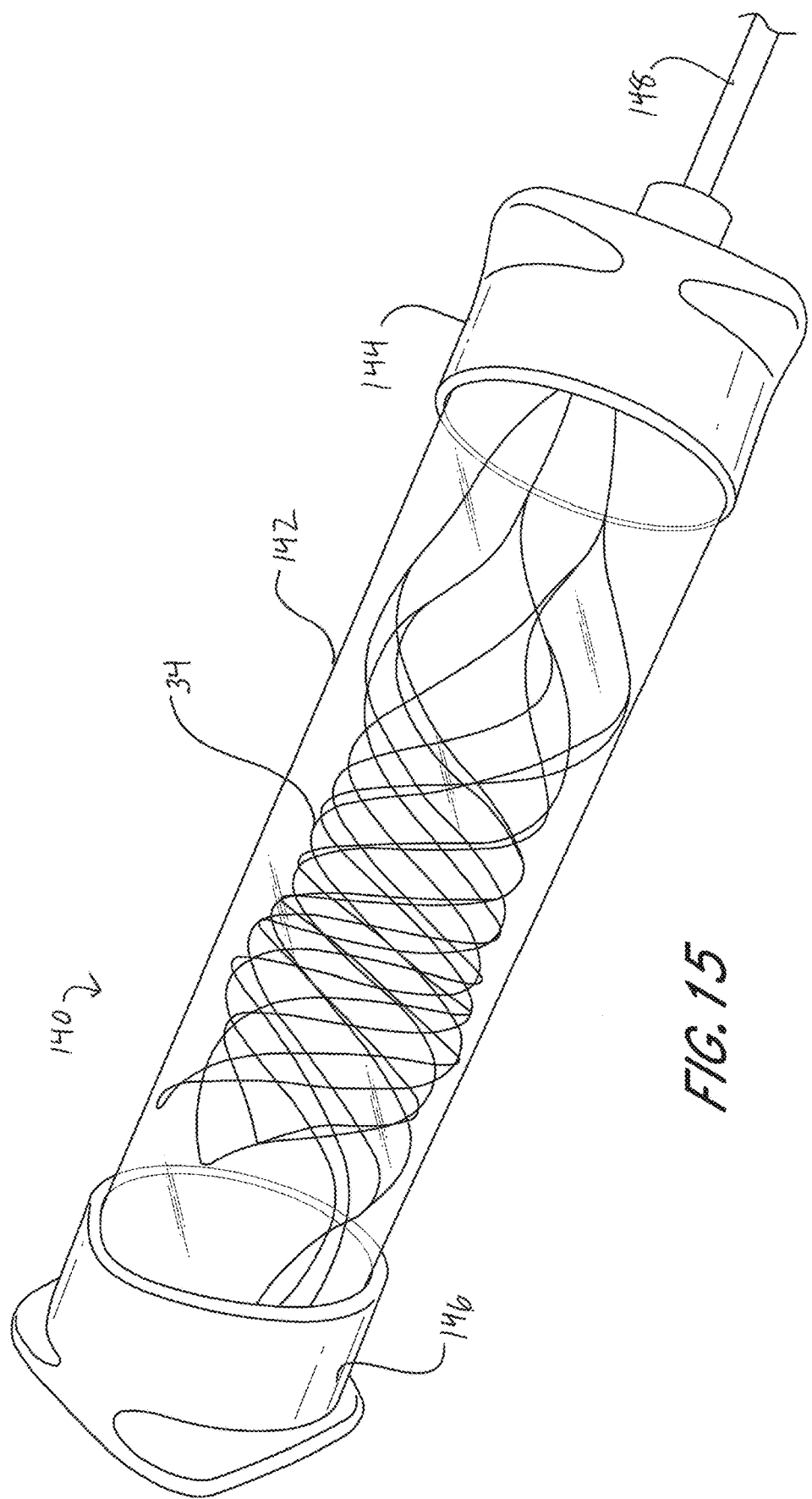
FIG. 15 is a perspective view of the wire frame of FIG. 14 in a hydration chamber.

One hydration chamber is shown in FIG. 15. The hydration chamber 140 comprises a sidewall 142 defining a water tight chamber therein for receiving a filter (illustrated as a frame 34 without the membrane). The sidewall 142 preferably has at least one transparent window to permit visual observation, and may be in the form of a transparent glass or plastic tube. A proximal end cap 144 and a distal end cap 146 are used to enclose the chamber. A tubular supply line 148 may be used to introduce a hydration media such as saline into the chamber, and also to carry the control wire 42. At least one of the end caps is removable to load and unload the chamber.

Figure 16:
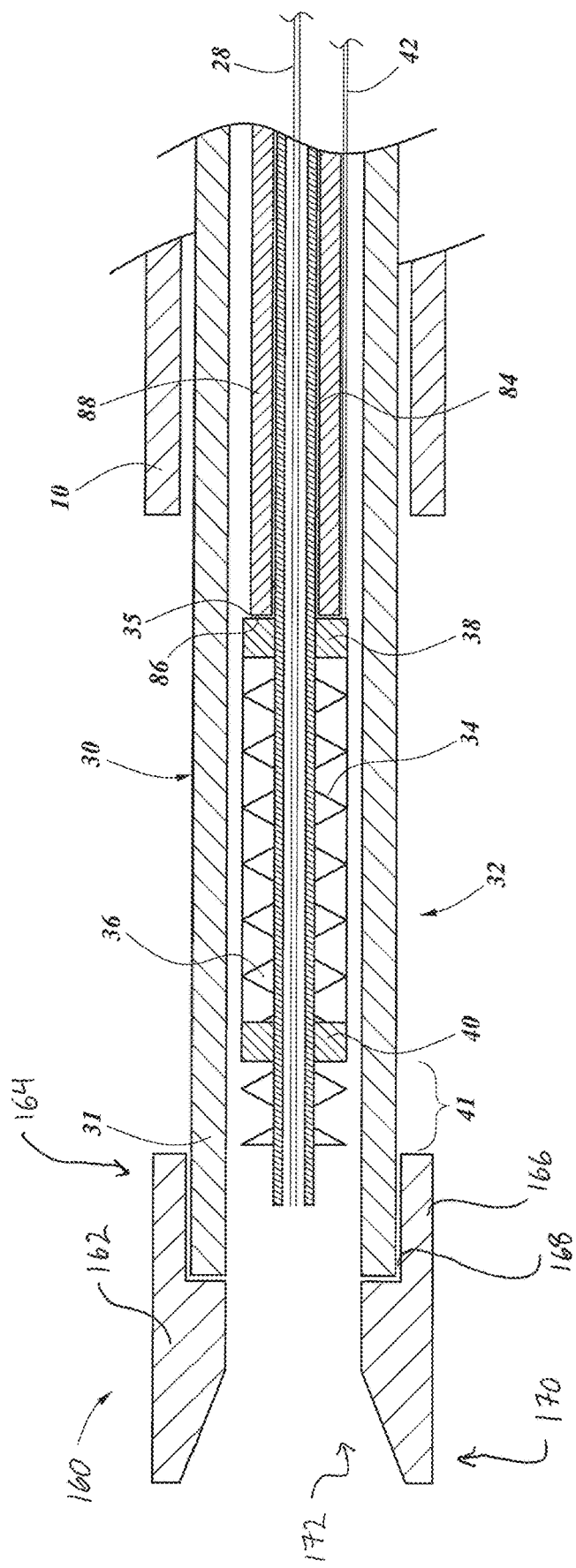
FIG. 16 is a side elevational view of a catheter as in FIG. 3, with a filter loader positioned on the distal end of the catheter.

Referring to FIG. 16, a filter loader 160 is attached to the distal tip of the delivery catheter 30, through which the inner push tube assembly, filter and control wire have been advanced into the delivery catheter 30. The filter loader 160 comprises a body 162 having a proximal end 164 configured for releasable attachment to the distal end of the tubular body 31. A coupling may be formed by an annular sidewall 166 defining an annular recess 168 for slidably receiving the distal end of the tubular body 31.

The distal end 170 of body 162 is provided with a ramped (e.g., conical) opening 172 in communication through the body 162 with the annular recess 168 and aligned with the tubular body 31 when mounted for use. The distal end of the ramped opening 172 is configured to receive an expanded filter. As the filter is advanced through the ramped opening, it is radially compressed sufficiently that it can be drawn proximally into the tubular body 31.

The inner push tube 88 and tip will be loaded through the delivery catheter 30 and the filter control wire 42 will be loaded through the delivery system and along side the inner push tube 88 and locked into the handle. After hydration of the filter, the catheter can be flushed through the side port. The inner push tube/tip and the filter wire can be pulled back on the handle, loading the filter and tip through the filter loader and into the delivery catheter 30. The filter loader may now be removed and the system is ready to be back-loaded onto the 0.035" guidewire and through the TAVR procedural sheath in the patient.

Multiple commercially available 0.035" guidewires may be used with the TAVR procedural catheter and the delivery catheter 30. Usually a stiff shaft to carry the large/bulky TAVR delivery system with a floppy tip for access over the arch and aortic valve crossing.

Alternatively, the catheter 30 may be provided in a "rapid exchange" configuration to remove dependence on an exchange length guidewire and its inherent difficulties. The proximal guidewire exit port may be positioned in the tip (distal to the elongated filter 32), or in the catheter side wall proximally of the filter 32 but in a distal portion of the catheter as is understood in the art.

A detachable handle allows physician control of the installation and repositioning of the frame/filter. A first portion of the handle is attached to the outer sheath 31/hemostatic valve and a second, extension portion is attached to the stainless steel support tube 84/push tube 88 assembly. The handle is attached and removed by engaging with an interrupted circular groove extending from the outer sheath 31 hemostatic seal housing, and turning the handle 90° relative to the hemostatic seal to engage or dis-engage the groove. The handle is attached and ready to use for installation of the frame and then removed after the filter is deployed to ease retraction of the frame.

Alternately a handle may not be needed and the stainless steel push tubing assembly with a small handle may be used to deploy the device.

Further, it is desired to have the nitinol encapsulated by the filter material by coating both the ID and the OD of the frame to improve adhesion, minimize exposed metal (thrombosis) and help integrity of the filter.

An example of a TAVR procedure utilizing a common access sheath with the embolic protection deployment catheter of the present invention is described below.

1. Place the TAVR procedural sheath (14 F ID) in the femoral artery over a 0.035" guidewire.
2. Open the F2 system package place the delivery system tray in the sterile field.
3. Fill the hydration chamber and hydrate the filter. Using flush port at proximal end of catheter, flush the catheter with saline.

4. Backload the F2 filter wire through the Filter loader and Delivery catheter 30 and pull the filter wire (filter) and the push tube (with tip) from the proximal end of the Delivery catheter 30 through the filter loader and into the Delivery catheter 30. Tip will seal distal end of catheter.
5. Introduce the Delivery catheter 30/tip over the 0.035″ guidewire (minimum of 260 cm length) through the hemostatic valve and into the TAVR procedural sheath. Advance the Delivery catheter 30 over the 0.035″ guidewire until the catheter marker is located in the desired landing zone in the ascending aorta.
6. At the proximal end of the F2 delivery system, you attach the delivery handle to the Delivery catheter 30 hemostatic valve. With the distal catheter marker in the desired landing location the operator will pin the filter wire/push tube and pull back the F2 outer sheath. First landing the filter where desired in the ascending aorta and then continuing to pull the outer sheath back until the filter is fully deployed in the aortic arch covering all three great vessels.
7. If the location in the aorta is not acceptable, the operator can pin the filter wire/push tube and push the F2 outer sheath over the filter to recapture and reposition.
8. The F2 catheter and push tube with tip can be removed, leaving the 0.035″ guidewire in place.
9. A pigtail catheter should be placed from the contralateral femoral artery, delivered through the F2 filter and be positioned in the non-coronary cusp of the aortic valve.

What is claimed is:

1. An intravascular filter for blocking passage of selected sizes of debris, comprising:
   a self expandable tubular wire frame, having a proximal end, a distal and a tubular sidewall; and
   a porous membrane carried by the tubular sidewall, the porous membrane having a distribution of pore sizes configured to block passage of selected sizes of debris;
   wherein a first group of pores has pores with a maximum dimension of no more than 25 microns and a second group of pores has pores with a maximum dimension of at least 50 microns, wherein the first group of pores is interspersed among the second group of pores, and a first prevalence of pores in the first group of pores is at least three times a second prevalence of pores in the second group of pores.

2. An intravascular filter as in claim 1, wherein the second group of pores will block particles greater than 120 microns.

3. An intravascular filter as in claim 2, wherein the second group of pores will block particles greater than 100 microns.

4. An intravascular filter as in claim 3, wherein the second group of pores will block particles greater than 80 microns.

5. An intravascular filter as in claim 1, wherein the first prevalence of pores in the first group of pores is at least four times the second prevalence of pores in the second group of pores.

6. An intravascular filter as in claim 1, wherein a pressure drop across the intravascular filter is less than 10 mm Hg at physiologic flow rates.

7. An intravascular filter as in claim 1, wherein a pressure drop across the intravascular filter is less than 5 mm Hg at physiologic flow rates.

8. An intravascular filter as in claim 1 wherein a sum of an area of all of the pores is at least 30% of a surface area of the porous membrane.

9. An intravascular filter as in claim 1 wherein a sum of an area of all of the pores is at least 35% of a surface area of the porous membrane.

10. An embolic protection system, comprising:
    a self expandable frame having a proximal end and a distal end;
    a filter membrane supported by the self expandable frame, wherein the filter membrane includes a distribution of different sized pores configured to filter debris throughout a length of the filter membrane that comprises a first group of pores and a second group of pores, wherein the first group of pores has a maximum dimension of no more than a first threshold and the second group of pores has a maximum dimension of at least a second threshold that is different than the first threshold, and wherein a first prevalence of pores in the first group of pores is at least three times a second prevalence of pores in the second group of pores in an unconstrained, expanded configuration;
    a leading frame segment extending distally beyond the filter membrane; and
    a transition between the self expandable frame and a control wire extending proximally from the transition;
    wherein the transition comprises a first set of wires extending proximally from the self expandable frame to a first set of welds, and a second, smaller set of wires extending proximally from the first set of welds, and the first set of welds are axially displaced from each other.

11. An embolic protection system as in claim 10, further comprising a tubular delivery catheter, and the self expandable frame is carried in a reduced cross-sectional configuration within the tubular delivery catheter.

12. An embolic protection system as in claim 11, wherein the tubular delivery catheter has an outer diameter of less than 14 F.

13. An embolic protection system as in claim 10, wherein the first threshold is 25 microns and the second threshold is 50 microns.

14. An embolic protection system as in claim 10, wherein the second group of pores will block particles greater than 120 microns.

15. An embolic protection system as in claim 14, wherein the second group of pores will block particles greater than 80 microns.

16. An embolic protection system as in claim 10, wherein the first prevalence of pores in the first group of pores is at least four times the second prevalence of pores in the second group of pores.

17. An embolic protection system as in claim 10, wherein a pressure drop across the filter membrane is less than 10 mm Hg at physiologic flow rates.

18. An embolic protection system as in claim 10, wherein a sum of an area of all of the pores is at least 30% of a surface area of the filter membrane.

19. An embolic protection system as in claim 10, wherein the filter membrane comprises electrospun fibers.

20. An intravascular filter as in claim 1, wherein the porous membrane comprises electrospun fibers.

* * * * *